US006897020B2

(12) United States Patent
Link et al.

(10) Patent No.: US 6,897,020 B2
(45) Date of Patent: May 24, 2005

(54) METHODS AND COMPOSITIONS FOR ELUCIDATING RELATIVE PROTEIN EXPRESSION LEVELS IN CELLS

(75) Inventors: Charles J. Link, Des Moines, IA (US); Tatiana Seregina, Ames, IA (US); Nicholas N. Vahanian, Ames, IA (US); James N. Higginbotham, Ames, IA (US); W. Jay Ramsey, Ames, IA (US); Bradley J. Powers, Ames, IA (US); Sachet A. Shukla, Ames, IA (US); Won Bin Young, Ames, IA (US)

(73) Assignee: NewLink Genetics Inc., Ames, IA (US)

( * ) Notice: Subject to any disclaimer, the term of this patent is extended or adjusted under 35 U.S.C. 154(b) by 0 days.

(21) Appl. No.: 09/811,842

(22) Filed: Mar. 19, 2001

(65) Prior Publication Data

US 2001/0034028 A1 Oct. 25, 2001

Related U.S. Application Data

(60) Provisional application No. 60/190,678, filed on Mar. 20, 2000, and provisional application No. 60/198,722, filed on Apr. 20, 2000.

(51) Int. Cl.$^7$ ................................................. C12Q 1/68
(52) U.S. Cl. ........................ 435/6; 435/69.1; 435/463; 435/320.1
(58) Field of Search .......................... 435/6, 69.1, 463, 435/320.1

(56) References Cited

U.S. PATENT DOCUMENTS

| | | | |
|---|---|---|---|
| 4,683,195 A | 7/1987 | Mullis | |
| 5,364,783 A | 11/1994 | Ruley et al. | |
| 5,434,065 A | 7/1995 | Mahan et al. | |
| 5,565,350 A | 10/1996 | Kmiec et al. | |
| 5,631,236 A | 5/1997 | Woo et al. | |
| 5,922,601 A | 7/1999 | Baetscher et al. | |
| 5,928,888 A | 7/1999 | Whitney | |
| 5,994,077 A | 11/1999 | Valdivia et al. | |
| 6,080,576 A | 6/2000 | Zambrowicz | |
| 6,096,717 A | 8/2000 | Jarvik | |
| 6,130,313 A | * 10/2000 | Li et al. | |
| 6,498,013 B1 | 12/2002 | Velculescu | |
| 2002/0025940 A1 | * 2/2002 | Whitney et al. | |

FOREIGN PATENT DOCUMENTS

| | | |
|---|---|---|
| EP | 0 761 822 A2 | 3/1997 |
| WO | WO 98/14614 A1 | 4/1998 |
| WO | WO 98/53319 A2 | 11/1998 |
| WO | WO 99/02719 | 1/1999 |
| WO | WO 99/50426 A1 | 10/1999 |
| WO | WO 0056874 A | 3/2000 |
| WO | WO 01/05970 A2 | 1/2001 |

OTHER PUBLICATIONS

Bejarano, Luis A., et al., "Motif Trap: A Rapid Method to Clone Motifs That Can Target Proteins to Defined Subcellular Localisations", Journal of Cell Science 112, 1999, 4207–4211, The Company of Biologists Limited 1999, Great Britain.

Bronchain, Odile J., et al., "A Gene Trap Approach in Xenopus", Brief Communication, Current Biology 1999, 1195–1198, Elsevier Science Ltd., Great Britain.

Dunn, Anne K., et al., "Aector for Promoter Trapping in Bacillus cereus", Gene 226, 1999, 297–305, Elsevier Science B.V., Great Britain.

Gygi, Steven P., et al., "Correlation Between Protein and mRNA Abundance in Yeast", Molecular and Cellular Biology, vol. 19, No. 3, 1999, 1720–1730, USA.

Hardouin, Nathalie, et al., "Gene–Trap–Based Taarget Site for Cre–Mediated Transgenic Insertion", Genesis 26, 2000, 245–252, Wiley–Liss, Inc., Canada.

Ishida, Yasumasa, et al., "RET: A Poly A–Trap Retrovirus Vector for Reversible Disruption and Expression Monitoring of Genes in Living Cells", Nucleic Acids Research, 1999, 1–11, Oxford Journals Online, Great Britain.

Mullen, Craig A., "Metabolic Suicide Genes in Gene Therapy", Pharmaceutical Therapy, vol. 63, 1994, 199–207, Elsevier Science Ltd., Great Britain.

Timmons, Lisa et al., "Green Fluorescent Protein/β–galactosidase Double Reporters for Visualizing Drosophila Gene Expression Patterns", Developmental Genetics 20, 1997, 338–347, Wiley–Liss, Inc., Canada.

Yeh, Edward, et al., "Green Fluorescent Protein As a Vital Marker and Reporter of Gene Expression in Drosophila", Proc. Natl. Acad. Sci., vol. 92, 1995, 7036–7040.

Zheng, Xiangqun H., et al., "An Avian Sarcoma/Leukosis Virus–Based Gene Trap Vector for Mammalian Cells", Journal of Virology, vol. 73, 1999, 6946–6952, USA.

Durick K. et al. "Hunting With Traps," Genome Wide Strategies For Gene Discovery and Functional Analysis, Genome Research 9 (11) 1019–1025 (1999).

Reddy, et al "Fluorescence Activated Sorting of Totipotent Embryonic Stem Cells Expressing Developmentally Regulated LacZ Fusion Genes," Proceedings of the National Academy of Sciences of USA 89 6721–6725 (1992).

Friedrich G., et al "41 Insertional Mutagenes By Retroviruses and Promoter Traps In Embryonic Stem Cells" Methods in Enzymology, Academic Press Inc, San Diego, CA, US. 225: 681–701 (1993).

(Continued)

Primary Examiner—James Ketter
Assistant Examiner—David A. Lambertson
(74) Attorney, Agent, or Firm—Howrey Simon Arnold & White, LLP

(57) ABSTRACT

The present invention relates generally to methods and compositions for the identification of differential protein expression patterns and concomitantly the active genetic regions that are directly or indirectly involved in different tissue types, disease states, or other cellular differences desirable for diagnosis or for targets for drug therapy.

22 Claims, 23 Drawing Sheets-

OTHER PUBLICATIONS

Alon U., et al "Broad Patterns of Gene Expression Revealed By Clustering Analysis of Tumor and Normal Colon Tissues Probed By Oligonucleotide Arrays," Proceedings of the National Academy of Sciences of USA. National Academy of Science, Washington, US 96: 6745–6750 (1999).

"Isolation of Differentially Expressed Genes By Combining Representational Difference Analysis (RDA) and CDNA Library Arrays," *Biotechniques, Eaton Publishing, Natick US* 25 (3) 434–438 (1998).

Altschul et al. (1997). Nucleic Acids Res. 25: 3389–3402.

Armentano et al. (1987). J. Virol. 61: 1647–1650.

Bender et al. (1987). J Virol. 61: 1639–1649.

Cormier et al. (1974). Bioluminescence in Coelenterates. Biochem. Biophys. Acta 346: 137–164.

Corpet et al. (1988). Nucleic Acid Res. 16: 10881–90.

Costa et al. (1998). Transcriptional regulation of the tissue-–type plasminogen activator gene in human endothelial cells: identification of nuclear factors that recognize functional elements in the tissue–type plasminogen activator gene promoter. European Journal of Biochemistry 258: 123–131.

Cytometry (1996). 23: 46.

Henikoff and Henikoff (1992). Proc. Natl. Acad. Sci. USA 89: 10915.

Higgins and Sharp (1988). Gene 73: 237–244.

Higgins and Sharp (1989). CABIOS 5: 151–153.

The human gene consortium. (2001). Nature 409: 860–921.

Huang et al. (1992). Computer Applications in the Biosciences 8: 155–65.

Fassati et al. (1998). Insertion of Two Independent Enhancers in the Long Terminal Repeat of a Self Inactivating Vector Results in High–Titer Retroviral Vectors With Tissue Specific Expression. Human Gene Therapy 9: 2459–2468.

Fleischmann et al. (1998). Cardiac Specific Expression of the Green Fluorescent Protein During Early Murine Embryonic Development. FEBS Letters 440: 370–376.

Fraser et al. (1997). Strategies for whole microbial genome sequencing and analysis. Electrophoresis 18: 1207–1216.

Goeddel et al. (1980). Nucleic Acid Res. 8: 4057.

J. Histochem. Cytochem. (1995). 43:77–83.

Lidberg et al. (1998). Transcriptional Regulation of Human Carboxyl Ester Lipase Gene in Exocrine Pancreas. The Journal of Biological Chemistry 273: 47.

Meyers and Miller (1988). Computer Applic. Biol. Sci. 4: 11–17.

European Search Report, dated Apr. 2, 2004.

Brenner, et al., "Analysis of mammalian cell genetic regulation in situ by using retrovirus–derived 'portable exons' carring the *Escherichia coli* lacZ gene", *Proc. Natl. Acad. Sci* , Jul. 1989, vol. 86, No. 14, pp. 5517–5521.

Stanford et al., "Expression Trapping: Identification of Novel Genes Expressed in Hematopoietic and Endothelial Lineages by Gene Trapping in ES Cells", *Blood*, 1998, vol. 92, No. 12, pp. 4622 to 4631.

Kerr et al., "Analysis of lipopoplysaccharide–response genes in B–lineage cells demonstrates that they can have differentiation stage–restricted expression and contain SH2 domains", *Proc. Natl. Acad. Sci.*, Apr. 1996, vol. 93, No. 9, pp. 3947–3952.

Tate, et al., "Capturing novel mouse genes encoding chromosomal and other nuclear proteins", *J. Cell. Science*, 1998, vol. 111, pp. 2575–2585.

Suarez, et al., "Green fluorescent protein–based reporter systems for genetic analysis of bactria including monocopy applications", *Gene* , 1997, vol. 196, Nos. 1–2, pp. 69–74.

Claverie and States (1993). Comput. Chem. 17: 191–201.

Miller et al. (1989). *Biotechniques* 7: 980–990.

Needleman and Wunsch (1970). *J. Mol. Biol.* 48: 443.

Ormerod (1994). *Flow Cytometry*: a practical approach. Second edition, IRL Press.

Paulus et al. (1996). Self–contained, tetracycline–regulated retriviral vector system for gene delivery to mammalian cells. *J. of Vrology* 70: 62–67.

Pearson and Lipman (1988). *Proc. Natl. Acad. Sci.* 85: 2444.

Pearson et al. (1994). *Methods in Molecular Biology* 24: 307–331.

Persing et al. (1993). *Diagnostic Molecular Microbiology: Principles and Applications. American Society for Microbiology, Washington, D.C.* (Table of Contents).

Post et al. (1981). *Cell* 24: 555–565.

Smith and Waterman (1981). *Adv. Appl. Math.* 2: 482.

Shapiro et al: (1995) *Practical Flow Cytometry*, Third Edition, Wiley–Liss.

Shimatake et al. (1981). *Nature* 292: 128.

Igarashi et al. (1998). A Novel Stategy of Cell Targeting Based on Tissue–Specific Expression of the Ecotopic Retrovirus Expression Gene. *Human Gene Therapy* 9: 2691–2698.

Valerie et al. (1998). Tissue Specific Cell Cycle Regulated Chimeric Transcription Factors for the Targeting of Gene Expression to Tumor Cells. *Human Gene Therapy* 9:2653–2659.

Medico et al (2001). A gene trap vector system for identifying transcriptionally responsive genes. *Nature Biotech.* 19: 579.

Wooten and Frederhen (1993). *Comput. Chem.* 17: 149–163.

Young and Link (2000). Chimeric Retroviral Helper Virus and Picornavirus IRES Sequence to Eliminate DNA Methylation for Improved Retroviral Packaging Cells. *J. Virol.* 74(11): 5242–5249.

Young et al. (2000). DNA Methylation of Helper Virus Increases Genetic Instability of Retroviral Vector Produce Cells. *J. Virol.* 74(7): 3177–3187.

Yu et al (1998). Coregulation of Tissue–Specific Alternative Human Carnitine Palmitovltransferase IB Gene Promoter by Fatty Acid Enzyme Substrate. *The Journal of Biological Chemistry* 273, No. 49.

Whitney et al (1998) A genome–wide functional assay of signal transduction in living mammalian cells. *Nature Biotechnology* 16:1329.

Jarvik et al (1996). CD–Tagging: A new approach to gene and protein discovery and analysis. *BioTechniques* 20: 896–904.

Skarnes et al (1995) Capturing genes encoding membrane and secreted proteins important for mouse development. *Proc. Natl. Acad. Sci USA* 92: 6592.

Zambrowicz et al (1998) Disruption and sequence identification of 2000 genes in mouse embryonic stem cells. Nature 392: 608–611.

\* cited by examiner

Natural genomic structure

Example Vector for Homologous Recombinations

Natural genomic structure

Transfection and integration of vector/s by illegitimate recombination

1bp added to change reading frame

2bp added to change reading frame

```
                                          Validation sequence/Splicing
                                          junction
                                             ┌──┐
  1 ttnnccgnga aagctcctcg cccttgctca ccatgggatg ccatttccta ggtctgcctc
                                     └──┘      └────────►
                                     NcoI      Gene trapped exon
                                     cloning site  of HMGI-C gene 61 ttggccgttt tctccaatg gtctctgctt tcttctgggc tgctttagag gggctcttgt 121 ttttgctgcc tttgggtctt cctctgggtc tcttaggaga gggctcacag gttggctctt 181 gctgctgctt cctgggtcgg ccgcgtcctc gcttctgtgg caccggggcg gcaggttgtc 241 cctgggctga tgtggacggc tgcccggcgc cctcaccgcg tgcgctcatc ctgcctcccg 301 ccgccgctac cactgcctct cttttttttt tttttttttt tttttgaaan ccccgggnnn 361 nnnnnnnnnn nnnnc      └──────────────────────┘ └──┘
                         Oligo-dT                EcoRI
                         primer                  cloning site
```

Fig. 20

```
                                        Validation sequence/Splicing
                                        junction
                                           ┌──┐
  1  tcngcgacca nctcctcgcc cttgctcacc atgggatgct cccggtggtg ggtcggtggt
                                     └──┘       └─────▶
                                     NcoI       Gene trapped-exon
                                     cloning site 61  ccctgggcag gggtctccaa atcccggacg agcccccaaa tgaaanaccc ccgtcntggg 121  tagtcaatca ctcagaggag accctcccaa ggaacagcga gaccactntt cggatgcana 181  cagcaagagg ctttattggg aatncgggta cccggcgac ncantctatc ngaagactgg 241  cgttattttt tttnttcttt tttttgaat tnccnggac anccnnctna gnntanctnc
     └──────────────────────────────┘ └────┘
              Oligo-dT                EcoRI
              primer                  cloning site 301  nctntnnnct nccctcctta cttctnntnt ntn
```

Fig. 21

METHODS AND COMPOSITIONS FOR ELUCIDATING RELATIVE PROTEIN EXPRESSION LEVELS IN CELLS

CROSS-REFERENCE TO RELATED APPLICATIONS

This application claims benefit under 35 U.S.C. §119(e) of provisional application No. 60/190,678 filed Mar. 20, 2000 and provisional application 60/198,722 filed Apr. 20, 2000.

FIELD OF THE INVENTION

This invention relates generally to the field of functional genomics. The invention enables the direct correlation of genomic DNA to rapidly quantifiable protein expression levels enabling a protein expression profile for a particular cell. This information can then be used to correlate with reference cells to identify differences in protein expression patterns that are responsible for differentiation, disease states, age, or any other temporal or spatial protein expression difference in particular cells for diagnosis, pathway regulation or drug target candidates.

BACKGROUND OF THE INVENTION

The last quarter of a century has been marked by a relentless drive by molecular biologists to decipher first genes and then entire genomes. Genomics, the use of genetic and molecular biology techniques to develop complete genome maps, as well as underlying genomic sequences for different organisms, has provided an explosion of information about the underlying genes which make up all living things. The fruits of this work already include the genome sequences of 599 viruses and viroids, 205 naturally occurring plasmids, 185 organaros, 31 new bacteria, 7 archea, 1 fungus, 2 animals and 1 plant (Nature, 409:860–921 (2001) The Human Gene Consortium). A significant milestone in the field of genomics culminated recently with the announcement that the entire human genome had been sequenced.

The most important application of this sequence data, however will be the ultimate identification of protein coding genes. Proteins are not produced directly from DNA, instead information in the form of DNA is transcribed to form messenger RNA (mRNA) molecules. These mRNA molecules function as templates for protein synthesis (translation). Each cell in the body contains the entire genome of the organism, however, only a portion of any cell's genome is expressed at any given time. Differences in expression profiles account for the different types of cells and tissues within an organism and for a cell's varying response to stress or disease.

Thus, cells in different tissue in the human body are unique because they have different native genes. For example, blood cells and muscle cells not only look different, they also perform different functions. Blood cells supply oxygen to organs and protect us from disease, while muscle cells enable us to move and digest food. These differences are due to specific gene products that are unique to blood or muscle cell proteins. The presence of different proteins within the same cell is the result of the function of different genes. An example could be the generation of Ab diversity or viruses.

Functional genomics is aimed at discovering the biological function of particular genes and uncovering the means by which sets of genes and their products work together in health and disease. According to the Human Gene Consortium group, there appear to be about 30,000 to 40,000 protein coding genes in the human genome. Amazingly this is only about twice as many as in *C. Elegans* or *D. melanogaster* the fruit fly. Thus the vast complexity of the human must be due to more complicated use of the existing genes with alternative splicing rather than simply increased number of genes.

If genes encode multiple proteins, then the architect of biological complexity distinguishing our genetic material from that of a worm is RNA, the molecule that directs the production of proteins from DNA. Unlike genes in bacteria, genes in plant and animal cells are not arranged as continuous DNA but as coding exons interspersed with noncoding introns making it possible to transcribe one gene into several different products as each mRNA is spliced together to form combinations of exons and bits and pieces of introns.

Previous estimates were that around 20% of human genes are transcribed in more than one alternative variant, but recent research puts the number closer to 50% and even this estimate has been criticized as conservative. For example, a team of American researchers studying genes that control brain development in *Drosophila melanogaster* reviewed calculations indicating that the Neurexin genes can give rise to 35,000 different possible protein products just from alternative splicing. If you add the possibilities for RNA editing as well as post translational modifications, one could potentially end up with millions of different gene products. In fact, studies of fly species that have evolved separately for millions of years show that sequences of many alternative splice sites are strictly conserved indicating that they are in fact used.

Thus the desired endpoint for the description of a biological system is not the analysis of mRNA transcript levels alone but also the accurate measurement of protein expression levels and their respective activities. Quantitative analysis of global mRNA levels is the current method for the analysis of the state of cells and tissues, (Fraser, et al, 1997 "Strategies for whole microbial genome sequencing and analysis" Electrophoresis 18:1207–1216). Several methods have been refined to provide absolute mRNA or relative mRNA levels in comparative analysis. mRNA based genomics, however provide several inherent limitations. For example, gene (mRNA) expression levels may not always accurately predict the protein expression levels. Therefore gene expression analysis such as with micro arrays, may not provide definitive information on certain targets. In fact Gygi et al, recently concluded that the correlation for all yeast proteins between mRNA and protein expression levels was less than 0.4. Indeed, for some genes, while the mRNA levels were of the same value the protein levels varied by more than 20-fold. Conversely, invariant steady-state levels of certain proteins were observed with respective mRNA transcript levels that varied by as much as 30-fold. Gygi et al. "Correlation between Protein and mRNA Abundance in Yeast" Molecular and Cellular Biology March 1999 pp 1720–1720.

Further, post translational modification of proteins such as proteolytic cleavage, glycosylation, phosphorylation, prenylation, myristalation, ubiquitination and N- and C-terminal processing can affect protein activity and half life. These modifications cannot be determined solely from gene sequence or expression data. Some proteins are active only when they are complexed to other molecules or proteins, or at a particular sub-cellular location within a cell. Again these factors cannot be determined from gene sequence expression data. FIG. 19 is a diagram demonstrating the layers of information which may be assayed to identify the real state of cell (furthest outward circle). Those who assay DNA and raw sequence data determine gene function based on sequence similarity, gene structure, and evolutionary relationships. Missing from this data is any mRNA or translational modification data. Those who assay mRNA gain a prediction of a protein profile based on the assumption that protein levels are directly proportional to mRNA. An assumption which is proving to be erroneous. Closest of all these methods to the real cell state is the method of the invention which detects actual cellular protein levels by direct measurement.

The field of study of proteomics has gained increasing importance as functional genomics attempts to assign functions to the mass of information from the human genome. Proteomics includes the science and processes of analyzing and cataloging all the proteins encoded by a genome (a proteome).

Complete descriptions of proteins including sequence structure and function will substantially aid the current pharmaceutical approach to therapeutics development. Thus the specific structural and functional aspects of a particular protein can be used to design better proteins or small molecule ligands that can serve as activators or inhibitors of protein function to develop drugs. Genome sequence information, due to the multitude of steps between gene transcription and corresponding protein function, is often insufficient to explain disease mechanisms.

Multiple genes may be involved in a single disease process. Identifying all the genes involved in a particular disease based on DNA sequence data may be possible but learning how these genes function in health and disease (and health therapeutic interventions can be designed for them) requires proteomics.

Disease may be caused by changes in gene expression, protein expression, or post translational modification of proteins. Many proteins are the intermediate targets for drugs, drug related changes in gene expression levels, or an indirect result of the drugs interaction with the protein. Cells and their proteomes are dynamic. One genome may yield multiple proteomes as a result of changes in differentiation, stress, or disease condition. Proteomics can be used to determine serum based biomarkers which can be valuable as clinical markers or used as a basis of a diagnostic.

As can be seen, a need exists in the art for identifying proteins and their concomitant coding sequences that are directly or indirectly regulated and involved in differential expression patterns associated with disease states, different tissue types, or other alternative cell states.

It is an object of the present invention to provide an immediate linking of protein information to its corresponding genome sequence to provide information for diagnostic protocols, pathway elucidation, or targets for drug design.

It is another object of the present invention to identify a protein expression profile of any particular cell, whether plant, bacterial, animal, etc. in origin, and to quantify relative levels of expression of those proteins associated with a particular population.

It is yet another object of the present invention to provide a library of functional genomic data that may be used to develop human therapeutics. Most researchers involved in the field of functional genomics rely on machine-based analysis for protein structure or function to assign functions to proteins. Those approaching the task from a sequencing objective assign function by analyzing and comparing genomic data developed by comparisons between disease and normal tissues. Typically this is accomplished through the use of gene chips or direct sequencing.

It is yet another object of the invention to provide an immediate link between genomic sequence to proteomic information using molecular biology techniques. Results of the information according to the invention can provide new therapeutic target development. Individual variations in protein expression levels between normal and aberrant tissues will lead to the direct identification of new therapeutic targets. If an unidentified protein is either higher or lower in expression levels within the malignant cells compared to the normal cells, it provides a probable target for further study and identifies a potential drug intervention site. Unique protein targets will be identified according to the invention.

It is yet another object of the invention to provide information about entire pathways of protein regulation, proving new target development when multiple proteins are involved in a particular state. Most cancer and other therapeutic drug development focuses on a single protein target at one time. However complex interactions between proteins result in the malignant or disease state in almost all cells. According to the invention, applicants method identifies protein expression levels for an entire pathway of active protein targets and can evaluate expression of multiple proteins simultaneously providing for analysis of pattern of protein co-expression with malignant or disease state cells as compared to normal cells.

BRIEF SUMMARY OF THE INVENTION

The present invention relates generally to methods and compositions for the identification of differential protein expression patterns and concomitantly the active genetic regions that are directly or indirectly involved in different cell types, tissue types, disease states, or other cellular differences desirable for diagnosis or for drug therapy targets.

According to the invention a method for obtaining a protein profile in a cell is disclosed by use of a genetic integration polynucleotide encoding a tag protein which may be actively detected. The polynucleotide construct comprises a marker gene or tag which is introduced into the genome of an organism using any vector insertion method known in the art, developed in the future, or described herein. The marker gene is not operably linked to any promoter sequence in the construct (promoterless) and the construct thus relies upon integration within an active transcription unit within the cell for expression. The activity of the tag is then measured to sort and preferably quantify protein expression patterns for the cell. Once a profile expression pattern is obtained, molecular biology techniques are employed to ascertain the particular genetic loci which is expressed. This information elucidates diagnostic profiles for disease or other cellular states or types as well as elucidating potential target sites for drug intervention and alternative gene forms (SNPs). FIG. 3 depicts a general overview of the process of the invention as applied to a cancer versus a normal cell.

Polynucleotides for achieving the methods of the invention are disclosed including expression constructs, molecular biology techniques, transformed cells, vectors, and methods of design of the same which are intended to be within the scope of the invention.

BRIEF DESCRIPTION OF THE DRAWINGS

FIG. 2A depicts a vector for exon acquisition. FIG. 2B depicts a vector designed for integration site acquisition. FIG. 2C depicts a vector for incorporation of multiple marker genes. FIG. 2D depicts a transfection cassette. FIG. 2E depicts a vector for replication competent virus. FIG. 2F depicts a vector for fusion protein marker for cell pre-separation and FACS analysis. RE Type IIS restriction enzyme site: LTR. long terminal repeat: CMV IE. CMV intermediate early promoter; NeoR; neomycin resistant gene; pA. bovine growth normone poly-A signal: SA. human gamma-globin intron #2 splicing acceptor; pA. NeoR. CMV. hrGFP. SA are in anti-sense orientatin against LTRs. Gag. pol. env. retroviral helper virus.

FIG. 4A is a schematic diagram of pGT5A plasmid. LTR. long terminal repeat; PBS. retroviral primer binding site: CMV IE. CMV intermediate early promoter; NeoR: neomycin resistant gene; pA. bovine growth hormone poly-A signal; SA. human γ-globin intron #2 splicing acceptor; AmpR. ampicillin-resistant gene for bacterial cloning. pA. NoR. CMV. hrGFP. SA are in anti-sense orientation against LTRs.

FIG. 5A is a schematic diagram of pGT5AH plasmid. LTR. long terminal repeat; PBS. retroviral primer binding site; CMV IE. CMV intermediate early promoter; NeoR. neomycin resistant gene; pA. bovine growth hormone poly-A signal; SA. human γ-globin intron #2 splicing acceptor; AmpR. ampicillin-resistant gene for bacterial cloning. pA. NeoR. CMV. hrGFP. SA are in anti-sense orientation against LTRs. His6 tag contains 6 continuous histidine residue at c-terminal of hrGFP for detection by anti-His6 antibody.

FIG. 6A is a schematic diagram of pGT5Z plasmid. LTR. long terminal repeat; PBS. retroviral primer binding site; CMV IE. CMV intermediate early promoter; NeoR; neomycin resistant gene; pA. bovine growth hormone poly-A signal: SA. human γ-globin intron #2 splicing acceptor; SD. synthetic splicing donor. SV40, simian virus type 40 early promoter. AmpR. ampicillin-resistant gene for bacterial cloning. pA. NeoR. CMV. hrGFP. SA are in anti-sense orientation against LTRs.

FIG. 7A depicts a construct of pGT5Z, which is derived from pGT5A with an insertion of a SV40 early promoter (SV40), Zeocin-resistant gene (ZeoR), and a synthetic splicing donor and partial intron to demonstrate the expected biological functions of pGT5A after gene trapping.

FIG 8A demonstrates that PA317 cells transfected with pGT5A showed a 3.6% of hrGFP-positive cell population.

FIG. 10A demonstrates A549 cells without transduction analyzed by FRCS.

FIG. 13A is a schematic diagram of serial gene trapping vectors with (α1.3-galactosyl transferase (α1.3-gal) gene. LTR. long terminal repeat; SV40. simian virus type 40 early promoter; ZeoR. Zeocin resistant gene; CMV. CMV early promoter; NeoR; neomycin resistant gene; pA. bovine growth hormone poly-A signal SA. human g-globin intron 2 splicing acceptor; SD. synthetic splicing donor pA. NeoR. CMV. α1.3 gal. SA or SD. ZeoR and SV40 are in anti-sense orientation against LTRs. FIG. 13B demonstrates gene trapping of pGT7A in A375/AMIZ cells. Cells were labeled with lectin conjugated with FITC for FACS analysis. Lectin binds to α1.3 gal epitopes on cell surface to show successful gene-trapping. FIG. 13C demonstrates gene trapping in A375/AMIZ cells 3 days post transfection of pGT7AH. FIG. 13D demonstrates that splicing function and functional α-1.3 α-gal/ZcoR fusion protein were demonstrated by lectin/FITC-positive cells.

To overcome this obstacle, a Type IIS restriction enzyme (RE) recognition site will be introduced between the SA signal and the start codon (ATG) of marker genes, such as hrGFP, alpha 1–3 galactosyltransferase (α-gal). etc. This can be illustrated as SA-RE-ATG. This RE site can be designed in frame with markers. After the SA joins to the splicing donor (SD) of the integrated cellular gene by cellular splicing mechanism, reverse transcription will be employed to convert this hybird RNA transcript into a complementary DNA (cDNA) (inclusive of, but not limited to, cDNA as cellular DNA may be used). This cDNA will then be subjected to RE digestion of exon from the integrated gene ten to twenty bases away from the SD/SA depending on which RE is used. A biotin-labeled primer #1 designed for a known marker (MK) gene is then employed to extend the ssDNA into this exon. Collection of this biotin-ssDNA by streptavidin conjugated magnetic beads will enrich these specific ssDNA for DNA terminal transferase reaction. Polymer deoxynucleotide can be added onto these ssDNA as a tail at their 3' end. A polymer primer complementary to the polymer tail and a second primer #2 on MK marker gene can therefore be used to amplify this 3'end of exon region. These short tags from different integrated genes by ligation reactions into a longer DNA fragment that is subsequently sequenced. Sequencing results of these tags can be used to retrieve the identity from EST databases or genomic databases. This approach can utilize all possible gene transfer methods to deliver above construct into DNA or RNA genomes of all organisms.

Figure 18A:
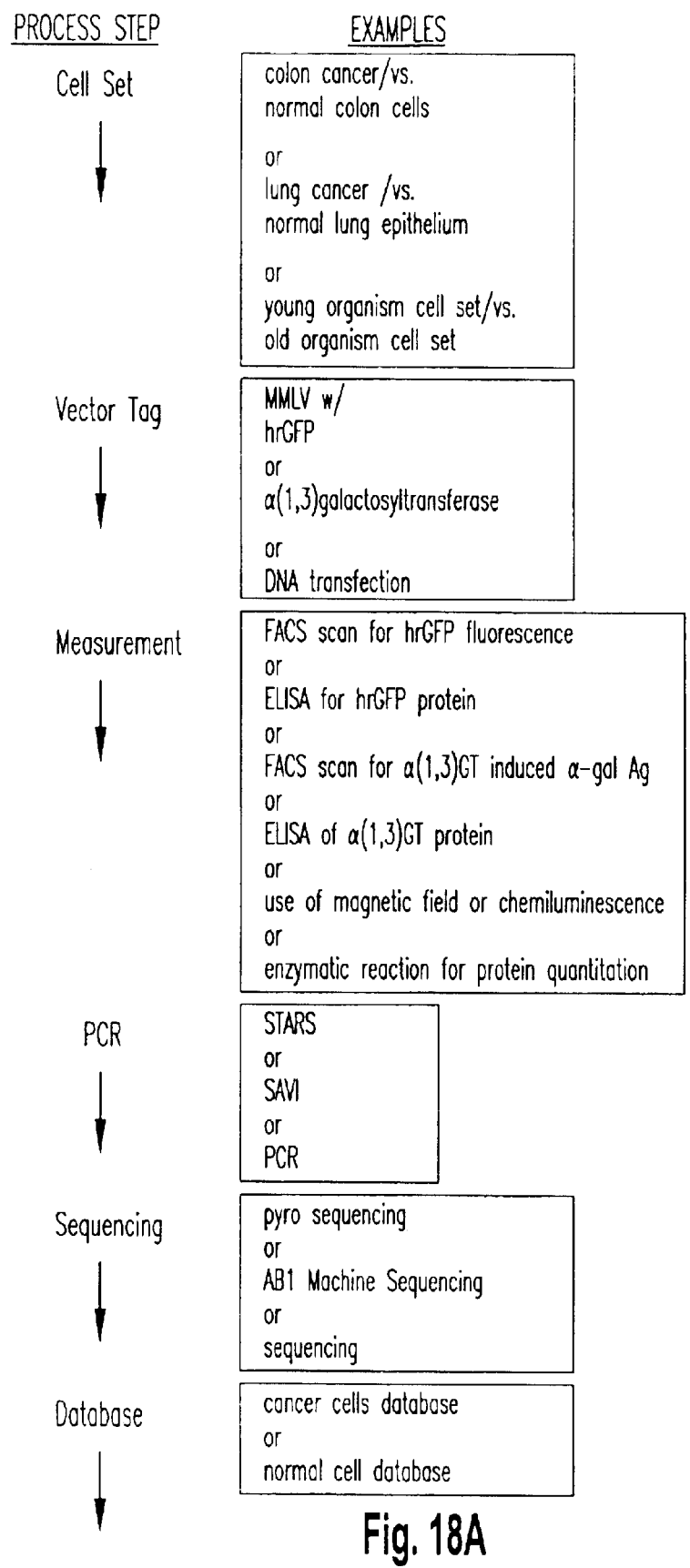

FIGS. 18A and B depict a non-limiting flow diagram demonstrating the entire process. This figure delivers a rudimentary overview of the process of the invention. The process begins with two different populations of cells to be compared. Each population of cells to be compared will have been marked genetically by a vector containing marker/s-peptides to facilitate detection and determination of relative concentration of marker/s. left portion of middle panel demonstrates separation of populations of cells based on relative amount of marker present in the tagged cells. Sequences flanking the vector will be determined by but not limited to serial analysis of viral integration (SAVI) or sequence tag acquisition and reporting system (STARS) methods. Valid tags will then be compared to public and commercial data bases and annotated into our own data bases. As can be seen at each stage alternatives exist for each step.

Figure 19:
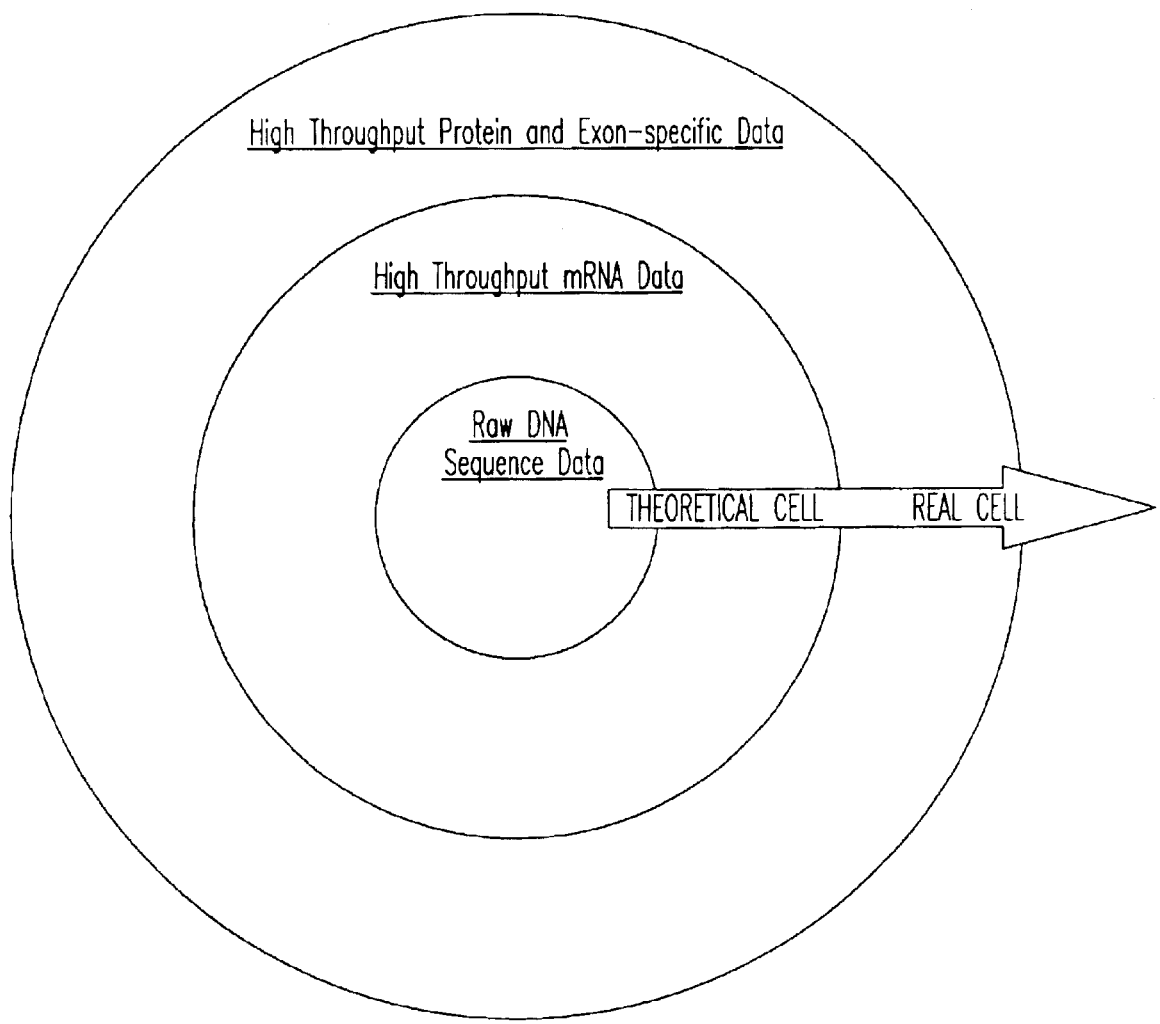

FIG. 19 is a diagram demonstrating the layers of information which may be assayed to identify the real state of cell (furthest outward circle). Those who assay DNA and raw sequence data determine gene function based on sequence similarity, gene structure, and evolutionary relationships. Missing from this data is any mRNA or translational modification data. Those who assay mRNA gain a prediction of a protein profile based on the assumption that protein levels are directly proportional to mRNA. An assumption which is proving to be erroneous. Closest of all these methods to the real cell state is the method of the invention which detects actual cellular protein levels by direct measurement.

FIG. 20 is a depiction of a successful gene trapping in pGT5A-transfected PA317 cells. NcoI restriction site located at the 5' end of hrGFP marker gene and an FcoRI at the Oligo-dA primer were used as cloning sites for gene trapped sequence into a sequencing vector which was digested with NcoI. After BLAST searching against mouse EST database in GenBank the sequence trapped by pGT5A demonstrates 99% homology to a high mobility group protein. HMGI-C. a nuclear phosphoprotein that contains three short DNA-binding domains (AT-hooks) and a highly acidic C-terminus.

Interest in this protein has recently been stimulated by three observations: the expression of the gene is cell-cycle regulated, the gene is rearranged in a number of tumors of mesenchymal origin and mice that have both HMGI-C alleles disrupted exhibit the pygmy phenotype. These observations suggest a role of HMGI-C in cell growth, more specifically, during fetal growth since the protein is normally only expressed in embryonic tissue. It is likely that the HMGI-C protein acts as an architectural transcription factor regulating the expression of one or more genes that control embtyonic cell growth. Since HMGI-C binds to the minor groove at AT-rich DNA this interaction could be a target for minor groove chemotherapeutic agents in the treatment of sarcomas expressing a rearranged gene.

FIG. 21 is a depiction of gene trapping of an exon with unknown biological function in pGT5A-transfected PA317 cells. NcoI restriction site located at the 5' end of hrGFP marker gene and an EcoRI at the oligo-dA primer were used as cloning sites for gene trapped sequence into a sequencing vector which was digested with NcoI and EcoRI. After BLAST searching against the EST database in GenBank, the sequence trapped by pGT5A is 95% match to a NCI_CGAP_Li9 Mus musculus cDNA clones, BF539247.1/ BF533319.1/...etc., which have been found in the cDNA libraries from Salivary gland and liver.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). As employed throughout the disclosure, the following terms, unless otherwise indicated, shall be understood to have the following meanings and are more fully defined by reference to the specification as a whole:

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA) See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term :antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "assay marker" or "reporter" refers to a gene product that can be detected in experimental assay protocol, such as marker enzymes, antigens, amino acid sequence markers, cellular phenotypic markers, nucleic acid sequence markers, and the like.

The term "assaying for the expression" of a protein coding sequence means any test or series of tests that permits cells expressing the protein to be distinguished from those that do not express the protein. Such tests include biochemical and biological tests and use either "selectable markers" or "assay markers."

As used herein, "chromosomal region" includes reference to a length of a chromosome that may be measured by reference to the linear segment of DNA that it comprises. The chromosomal region can be defined by reference to two unique DNA sequences, i.e., markers.

A "cloning vector" is a DNA molecule such as a plasmid, cosmid, or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a selectable marker gene that is suitable for use in the identification and selection of cells transformed with the cloning vector. Selectable marker genes typically include genes that provide tetracycline resistance or ampicillin resistance.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W. H. Freeman and Company.

The term "detectable marker" encompasses both the selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed.

An "expression vector" is a DNA molecule comprising a gene that is expressed in a host cell. Typically, gene expression is placed under the control of certain regulatory elements including promoters, tissue specific regulatory elements, and enhancers. Such a gene is said to be "operably linked to" the regulatory elements.

The term "expression system" is used herein to refer to a genetic sequence which includes a protein encoding region which is operably linked to all of the genetic signals necessary to achieve expression of the protein encoding region. Traditionally, the expression system will include a regulatory element such as a promoter or enhancer, to increase transcription and/or translation of the protein encoding region, or to provide control over expression. The regulatory element may be located upstream or downstream of the protein encoding region, or may be located at an intron (noncoding portion) interrupting the protein encoding region. Alternatively it is also possible for the sequence of the protein encoding region itself to comprise regulatory ability.

The term "functional splice acceptor" refers to any individual functional splice acceptor or functional splice acceptor consensus sequence that permits the construct of the invention to be processed such that it is included in any mature, biologically active mRNA, provided that it is integrated in an active chromosomal locus and transcribed as a contiguous part of the premessenger RNA of the chromosomal locus.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "host cell" encompasses any cell which contains a vector and preferably supports the replication and/or expression of the vector. Host cells may be prokaryotic cells such as *E. coli*, or eukaryotic cells such as yeast, insect, amphibian, or mammalian cells. The term as used herein means any cell which may be in culture or in vivo as part of a unicellular organism, part of a multicellular organism, or a fused or engineered cell culture.

The term "internal ribosome entry site" (IRES) is an element which permits attachment of a downstream coding region or open reading frame with a cytoplasmic polysomal ribosome for purposes of initiating translation thereof in the absence of any internal promoters. An IRES is included to initiate translation of selectable marker protein coding sequences. Examples of suitable IRESes that can be used include the mammalian IRES of the immunoglobulin heavy-chain-binding protein (BiP). Other suitable IRESes are those from the picornaviruses. For example, such IRESes include those from encephalomyocarditis virus (preferably nucleotide numbers 163–746), poliovirus (preferably nucleotide numbers 28–640) and foot and mouth disease virus (preferably nucleotide numbers 369–804). Thus, the viruses are located in the long 5' untranslated regions of the picornaviruses which can be removed from their viral setting in length to unrelated genes to produce polycistronic mRNAs.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The term "polymerase chain reaction" or "PCR" refers to a procedure described in U.S. Pat. No. 4,683,195, the disclosure of which is incorporated herein by reference.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

The term "primer" refers to a nucleic acid which, when hybridized to a strand of DNA, is capable of initiating the synthesis of an extension product in the presence of a suitable polymerization agent. The primer preferably is sufficiently long to hybridize uniquely to a specific region of the DNA strand.

As used herein "promoter" includes reference to a region of DNA upstream from the start of transcription and involved in recognition and binding of RNA polymerase and other proteins to initiate transcription.

The term "promoterless" refers to a protein coding sequence contained in a vector, retrovirus, adenovirus, adeno-associated virus or retroviral provirus that is not directly or significantly under the control of a promoter within the vector, whether it be in RNA or DNA form. The vector, plasmid, viral or otherwise, may contain a promoter, but that promoter cannot be positioned or configured such that it directly or significantly regulates the expression of the promoterless protein coding sequence.

The term "protein coding sequence" means a nucleotide sequence encoding a polypeptide gene which can be used to distinguish cells expressing the polypeptide gene from those not expressing the polypeptide gene. Protein coding sequences include those commonly referred to as selectable markers. Examples of protein coding sequences include those coding a cell surface antigen and those encoding enzymes. A representative list of protein coding sequences include thymidine kinase, β-galactosidase, tryptophane synthetase, neomycin phosphotransferase, histidinol dehydrogenase, luciferase, chloramphenicol acetyltransferase, dihydrofolate reductase (DHFR); hypoxanthine guanine phosphoribosyl transferase (HGPRT), CD4, CD8 and hygromycin phosphotransferase (HYGRO).

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, virus, or nucleic acid fragment. Typically, the recombinant expression cassette portion of an expression vector includes, among other sequences, a nucleic acid to be transcribed, and a promoter.

A "recombinant host" may be any prokaryotic or eukaryotic cell that contains either a cloning vector or an expression vector. This term also includes those prokaryotic or eukaryotic cells that have been genetically engineered to contain the clone genes in the chromosome or genome of the host cell.

The terms "recombinant virus vector" refers to any recombinant ribonucleic acid molecule having a nucleotide sequence homologous or complementary with a nucleotide sequence in an RNA virus that replicates through a DNA intermediate, has a virion RNA and utilizes reverse transcriptase for propagation of virus in a host cell. Such viruses can include those that require the presence of other viruses, such as helper viruses, to be passaged. Thus, retroviral vectors or retroviruses are intended to include those containing substantial deletions or mutations in their RNA.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The terms "tag" or "tagged" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, 131I), fluorescent labels (e.g., FITC, rhodamine, lanthanide phosphors), enzymatic labels (or reporter genes) (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "translational stop sequence" refers to a sequence that codes for the translational stop codons in three different reading frames. This translational stop sequence is physically located downstream (3') of the splice acceptor sequence, but upstream (5') of the selectable marker fusion protein translation initiation site. It causes truncation of the peptide chain encoded by exons upstream of the retroviral vector at the chromosomal locus. It also prevents the translational reading frame of the genomic locus from proceeding into the selectable marker gene of the invention, thus preventing potential translation of it in a non-sense reading frame.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244 (1988); Higgins and Sharp, CABIOS 5:151–153 (1989); Corpet, et al., *Nucleic Acids Research* 16:10881–90 (1988); Huang, et al., *Computer Applications in the Biosciences* 8:155–65 (1992), and Pearson, et al., *Methods in Molecular Biology* 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et a., *Nucleic Acids Res.* 25:3389–3402 (1997). Software for performing BLAST analyses is publicly available, e.g., through the National Center for Biotechnology-Information. This algorithm involves first identifying high scoring sequence pairs (HSPs) by identifying short words of length W in the query sequence; which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, ore preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial Identity" in the context of a peptide indicates that a peptide comprises a sequence with at least 70% sequence identity to a reference sequence, preferably 80%, ore preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). an indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

The invention relates to a method for identifying a particular protein profile for a cell that can be used for diagnosis or as a target site for a drug. According to the invention activity at specific genetic loci is correlated with the functional state and/or concentration of product proteins in a test cell and is then compared to a reference cell for elucidation of differential and quantitative protein expression profiles.

The method can be used to identify gene or gene products associated with a biological process or state of interest, to identify proteins including entire pathways of expression associated with a particular state, to screen cells for the identification of a particular protein profile that is associated with said state for diagnosis, to identify novel proteins associated with particular cell types or states, or even to identify polymorphisms in genes causing differential proteins between genes. This can include the assay for expression or not of a particular protein or a relative quantitative expression profile.

The method employs three basic steps to achieve its objective. First the test cell is transformed with a promoterless polynucleotide construct to "tag" the cell by integration of a detectable marker or reporter nucleotide sequence in the genome of the cell. The detectable marker sequence encodes a protein that is only produced when the integration event has occurred in a cellular gene in such a fashion that the marker protein is produced under the transcriptional control of a cellular gene promoter, resulting in an interrupted gene product and preferably a fusion protein incorporating the tag.

This is achieved by inclusion of the marker nucleotide sequence in a polynucleotide construct, typically a vector, with no promoter operably linked to the marker nucleotide sequence. Thus expression of the marker is dependent upon initiation of transcription from the target cell genome. Any vector can be used according to the invention which is capable of integrating into the genome of said target cell, this can include but is not limited to, e.g., parvoviruses, foamy viruses, retrotransposons, etc., and/or naked DNA). In a preferred embodiment the vector is a defective retrovirus, packaging of the defective retroviral genome and insertion of the defective retroviral genome via abortive infection into the DNA of the cells to be analyzed.

Production of the marker indicates that the construct has been integrated into an actively transcribed region of the cellular genome and production/accumulation of the marker protein becomes dependent upon transcription initiated at cellular promoters.

In the second step of the invention, cells containing integrated sequences can be sorted and fractionated on the basis of the expression of the marker protein. Again any of a number of different sorting methodologies can be used depending on the chemical physical or mechanical characteristics of the marker gene. In a preferred embodiment the marker is a fluorescent protein and quantitation of protein is performed by Fluorescence Activated Cell Sorting (FACS) such that in addition to quantifying protein, cells expressing given levels of protein may be sorted and collected in fractions (there may be any number of fractions, eg. 5, 10, 20, 25, 50, 100, etc., depending upon the desired level of resolution). In addition other means such as the use of ferrous metal conjugates and electromagnetic force can be used for expression-dependent fractionation of cells.

The high speed and resolution of the invention allow for the first time, real time analysis of molecular pathways of activation including but not limited to signal transduction via phosphorylation levels of targets (ie direct measurements of phosphatases/kinases and/or production of cyclic AMP). The invention also provides analysis of gated and non gated channels to monitor signaling via $Ca^{2+}$, $Mg^{2+}$, $Zn^{2+}$, pH and other trace elements. This analysis can also monitor protein-protein interactions as well using fluorescent Ab, fluorescent Ag, fluorescent ligand, fluorescent receptor, fluorescent substrates or non-fluorescent substrates that become fluorescent after enzymatic cleavage/activation or even conventional chlorometric enzyme-substrate based reactions. The combination of speed and precision offered by FACS has not been fully demonstrated using other methods of analysis, however other methods may be used. In another embodiment electromagnetic forces can also be used to separate and quantitate cells by the expression of the marker gene product.

In the final step, once sorted into subpopulations (based upon the level of marker peptide expression) DNA, RNA, and/or protein are isolated from the cells in each subpopulation and analyzed. This analysis includes determination of the cellular DNA sequences into which the marker DNA has been inserted. Then comparison is made against a reference cell to identify differential protein expression that is correlated with a particular state, for example a disease state such as cancer for use as a diagnostic or to identify a potential target for drug intervention.

Rather than isolating and amplifying each individual cell which has acquired an integrated and expressed marker tag and then subsequently analyzing the site of insertion and the level of protein expression, estimates of these values may be obtained by analyzing statistically significant numbers of cells with such integrants that have been clustered together by virtue of demonstrating an approximately equivalent level of gene expression.

For example, if in a population of 1,000,000 cells, 10,000 cells with integration events analyzing a series of different genes in a population demonstrate a mean marker peptide concentration of value x, where x represents the mean marker peptide concentration seen in the first percentile of cells detected to have any expression of the marker peptide. If integration sites are determined in any (or all) of these cells, the genes where they have integrated are said to be expressed in the lowest percentile of detectable expression. This can be said independent of any knowledge that relates a specific integration event in a specific gene in a specific clone of cells to a specific protein level. By applying appropriate statistical methods and examining a large enough number of integration events, the need to obtain and analyze specific clones is obviated for the purpose of determining relative levels of protein expression from a given genetic locus.

In further embodiments the differential expression data can be used with statistical methods to assign marker peptide expression levels for each interrupted gene. In further yet embodiments a database which incorporates this newly generated data, with other data sources, is combined to produce a record on the relationship of gene expression (at the RNA and protein level) to the function of the cell can be generated. In cases where the cells under study can be obtained in both cancerous and normal conditions, comparisons of the relative gene expression can be used to identify genes which can serve either as diagnostic markers of pathology or as sites of pharmacologic intervention for treatment of cancer. Similarly, other diseases can be analyzed merely by substituting the source of cells for analysis.

Figure 18B:
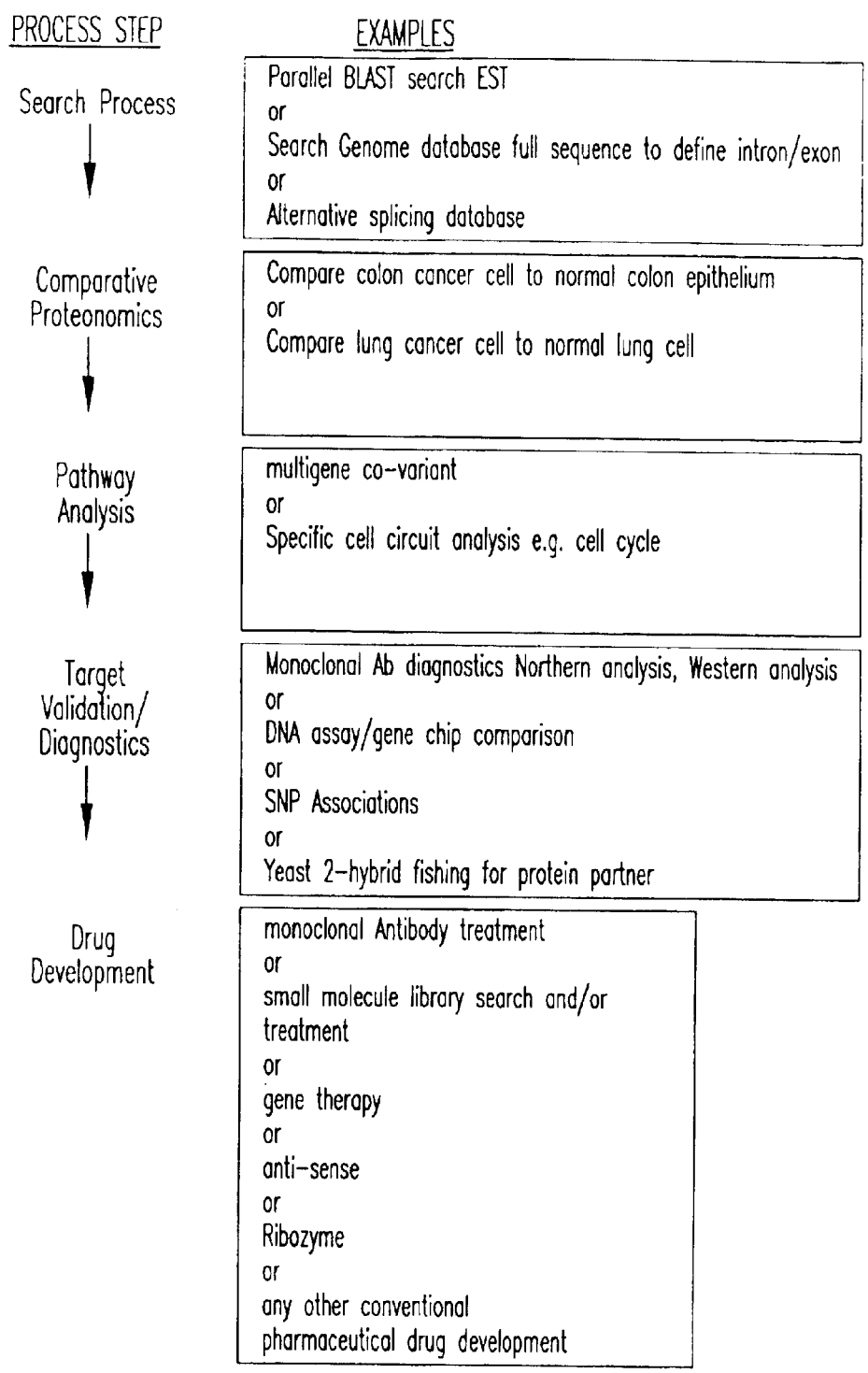

Each of the foregoing steps will now be described in more detail below. It is understood that for each step numerous expedients may be employed as well as alternative molecular biology techniques currently or yet to become available which achieve the same results. Choice of reaction agents, protocols etc is considered nothing more than routine optimization of experimental parameters based upon the teaching herein and are intended to be within the scope ot the invention. FIG. 18 is a flow diagram depicting an overview of the process including several specific examples of alternatives available for each step.

Identification and Selection of Test and Reference Cell Types

According to the invention a comprehensive protein profile is generated from any cell type of interest. A test cell can be any cell, or portion thereof with genetic material. A reference cell can be any cell type the difference in protein expression patterns and levels is desired to be measured against. Preferably the cells are maintained as similar to their native state as possible and culture techniques, incubation times etc. are performed identically between the two to minimize any non-naturally occurring differences. For example, development of the comprehensive protein profiles of pre-cancerous, and malignant test cells and a normal reference cell could be achieved according to the invention. Such identifiers of protein signatures will characterize molecular events of tumor development and cellular mechanisms involved.

Recent initiatives in identification of molecular fingerprints of tumors have been focused on studies of DNA and mRNA levels. These studies indicate that gene expression paths in two tumor samples from the same individual were almost always more similar to each other than either was to any other sample and that tumors could be classified in subtypes distinguished by differences in their gene expression patterns.

According to the invention, a test cell and a reference cell could be obtained from the same patient to get a individual protein fingerprint that can be used to diagnose or treat that patient. For example when a tumor is excised, often a margin of nontransformed cells is removed as well. Protein profiling can help to ensure that the cells removed all had similar profiles to normal cells rather than the metastatic cells from the same patient.

Comparisons may be made according to the invention from different cancers (e.g. lung, breast, colon, melanoma), different stages of malignant progression from corresponding normal tissue to highly malignant primary site and/or metastatic site, tumors caused by endemic/local agents (e.g. environmental agents (asbestos, infectious agents), tissues surrounding the incipient tumor (e.g. blood cells), extracts from body fluids (e.g. cancer cells of the urinary tract may be shed into urine), and tumors from species other than human.

One example of cell lines that may be used as test cells include human tumor cell lines. For example human tumor cell lines representing a broad spectrum of human tumors and exhibiting acceptable properties and growth characteristics may be grown according to standard operating procedure for cell line expansion, cryopreservation and characterization. Examples of human cancer cell lines which may be used according to the invention include: Lung Cancer Human Cell Lines (Non-small cell lung cancer adenocarcinoma cell line, A549; adenosquamous cell carcinoma, NCI-H125; squamous cell carcinoma, SK-MES-1, bronchial-alveolar carcinoma, NCI-M322; large cell Carcinoma, A 427, mucoepidermoid carcinoma, NCI-M292, small cell lung cancer (SCLC) "Classic", NCI-M69; SCLC "Variant", NCI-M82; SCLC "Adherent", SHP77; colon cancer human cell lines (COLO 205, DLD-1, HCT-15, HT29, LoVo); breast cancer human cell lines, (MCF7 WT, MCF7 ADR, MDA-MB-231, HS 578T); prostate cancer human cell lines (D4 145, LNCaP, PC-3, UMSCP-1); melanoma human cell lines (RPMI-7951, LOX, SK-MEL 2, SK-MEL-5, A 375); renal cancer human cell lines (A 498, A 704, Caki-1, SNI2 C, UO-31); ovarian cancer human cell lines (IGROV-1, OVCAR-3, SK-OV-3, A2780, OVCAR-4, OVCAR-5, OVCAR-8); leukemia human cell lines (Molt-4, RPMI 8336, P388, P388/ADR-Resist CCRF-CEM, CCRF-SB); central nervous system cancer human cell lines (SF 126, SF 295, SNB19, SNB 44, SNB 56, TE 671, 4251); sarcoma human cell lines (A-204, A 673, MS 913T, Ht 1080, Te 85); head and neck squamous cancer human cell lines (UM-SCC-MB,C, UM-SCC-21A, UM-SCC-22B); normal fibroblasts (MRC-5-lung, human, CCD-194Lu-lung, human, IMR-90-lung, human, NIH 3T3-mouse, embryo).

Another example of cell types which could be used includes primary cells derived from normal or cancer tissue specimens such as a tissue specimen obtained from normal and/or cancerous tissue that is disaggregated using dissociating enzymes and single cell suspension that is enriched, purified and characterized using MACS tumor cell reagents.

In yet another embodiment test and reference cells can be used to develop protein profiles associated with aging such as different stages of ontogenesis, for example protein profiles of embryonic liver-derived hematopoietic stem cell (HSC) vs. cord blood HSC vs. young adult HSC vs. old age organism-derived HSC.

In yet another embodiment protein profiles of cells from Neurodegenerative diseases which as patients with Alzheimer's disease, Parkinson's disease may be assayed.

In yet another embodiment profiles may be obtained for other age-related conditions such as male pattern baldness.

In yet another embodiment protein profiles can be obtained from human pathological conditions such as genetic diseases (inborn errors of metabolism: Adenosine deaminase deficiency, cystic fibrosis, Duchenne's muscular dystrophy).

In yet another embodiment protein profiles may be obtained for multifactorial and somatic genetic diseases (hypertension, coronary artery disease, obesity, diabetes mellitus)

In yet still another embodiment profiles may be obtained for other non-genetic diseases (AIDS and other infectious diseases)

In yet still another embodiment profiles may be obtained for autoimmune disorders (rheumatoid arthritis, systemic lupus erythematosus, multiple sclerosis, etc.)

In yet another embodiment profiles may be obtained for human non-disease traits such as physical traits (athletic abilities, visual acuity); cognitive and personality traits (musical ability, cognition, memory, male-pattern-baldness)

In yet another embodiment two cells of the same type may be assayed to identify alternative gene forms, such as polymorphic loci etc.

Further, as can be seen, any cell type can be used according to the invention including but not limited to, microorganisms, plants, invertebrates, vertebrates, and mammals.

Integration of Assay Marker Peptide-encoding Sequences into the Genetic Material of Test and Reference Cells According to the invention the process begins by the insertion of an assay marker DNA sequence into the genome of a test cell to be analyzed. This assay marker sequence includes any expressed molecule which can be screened in a defined assay system such that the cells may be identified, selected, sorted and/or preferably quantified, based upon the expression of the marker sequence. In a preferred embodiment this marker sequence or (tag) will be a chromophore which will fluoresce (such as humanized rellina green fluorescence protein). Other examples of assay marker sequences which may be used according to the invention include α-1-3 galactosyltransferase, sodium/iodine symporter, (or viral envelope protein could be used). Still other marker systems include but are not limited to any detectable cell surface displayed protein; other markers can be used such as lipid, lipoprotein, glycolipid, and glycoprotein targets that can be tagged with specific fluorescent compounds using labeled antibodies, direct chemical linkage and/or combination of direct and indirect tagging.

The marker peptide/fusion protein may be intracellular and dispersed throughout the cytoplasm or localized to specific intracellular compartments by leader sequences present on the marker peptide/fusion proteins(s). The marker peptide(s) can be incorporated into a single protein or into macromolecular complexes in which several different proteins (derived from multiple cellular genes) are linked by specific molecular interactions that demonstrate a unique fluorescent profile.

The marker peptide is only produced when the integration event has occurred in a cellular gene in such a fashion that the marker protein is produced under the transcriptional control of a cellular gene promoter. This is achieved by inclusion of the marker DNA sequence within a promoterless expression construct.

In a preferred embodiment the expression construct is included within an appropriate gene transfer vehicle which is then used to transduce cells to express the marker gene by the recipient host test cells. The gene delivery vehicle can be any delivery vehicle known in the art and can include simply naked DNA which is facilitated by a receptor mediated transfection or via homologous recombination. (see FIG. 14). In a homologous recombination embodiment a vector is engineered to have highly repeated sequences such as Alu flanking the assay marker gene so that recombination is facilitated at the repetitive sites causing integration of the nucleotide. Any of a number of vectors can be used, such vectors include but are not limited to eukaryotic vectors, prokaryotic vectors (such as for example bacterial vectors) and viral vectors including but not limited to retroviral vectors, adenoviral vectors, adeno-associated viral vectors, lentivirus vectors (human and other including porcine), or any other vector which will stably integrate into the host cell genome.

Figure 13A:
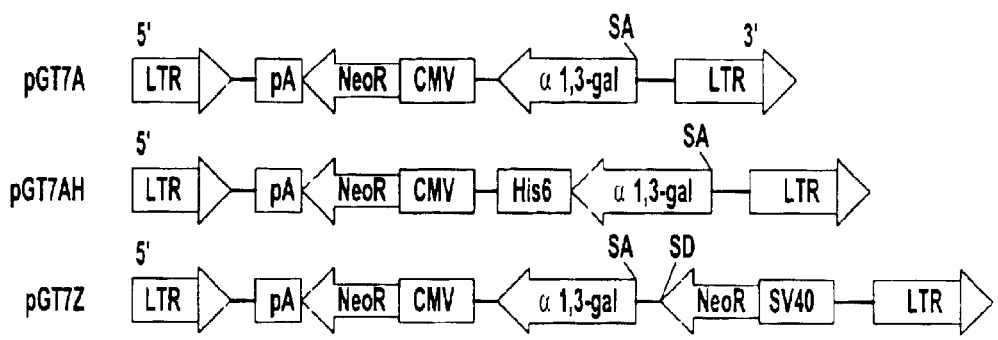
FIGS. 13A–D depict gene trapping with an α1.3-galactosyl transferase as a reporter gene in human melanoma cell line. A375.
Figure 13B:
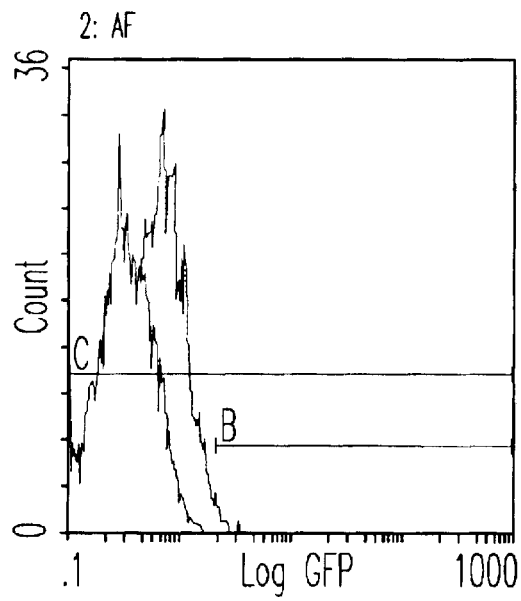
Figure 13C:
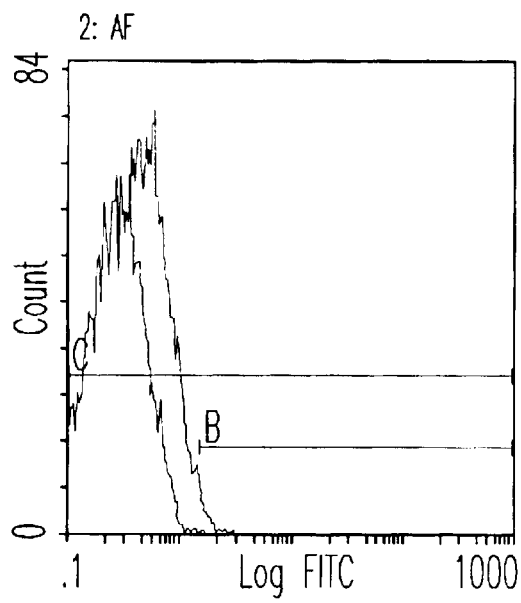
Figure 13D:
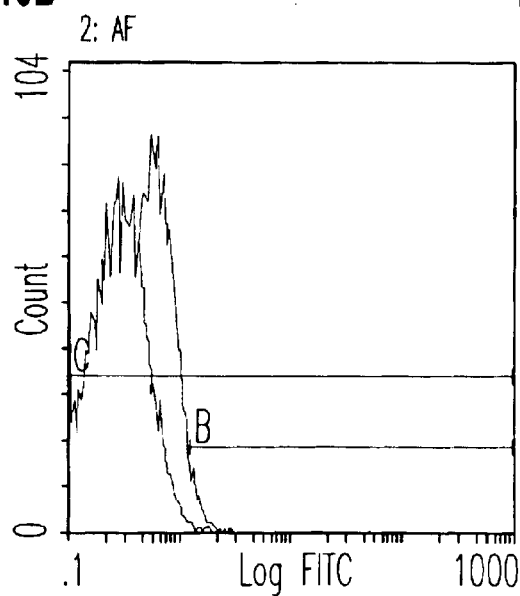

The preferred embodiment of the application will use vectors (DNA, RNA, DNA/RNA hybrids etc.) that contain markers which may be sorted to include but not limited to cell surface displayed or cytoplasmic protein; lipid, lipoprotein, glycolipid, and glycoprotein targets that can be tagged with specific fluorescent, chemiluminescent, or bioluminescent compounds using labeled antibodies, direct chemical linkage and/or combination of direct and indirect tagging. Data supporting this claim is seen in FIG. 13(C). These vectors will use the processes of illegitimate recombination, homologous recombination, and/or viral vectors to integrate said markers into the genomic DNA of target cells (the integrated vector serves as a molecular bar code). Alu sequences are approximately 300 bp in length and are found on average every 3000 bp in the human genome. Alu or other highly repetitive sequences can be used to induce homologous recombination for insertion of the marker gene. The vectors will be delivered to the target cells via standard gene delivery methods to include but not limited to lipid mediated transfection (cationic, anionic, and neutral charged), activated dendrimers (PolyFect® Reagent, SuperFect® Reagent {Qiagen}), Pethyleneimene (PEI), receptor mediated transfection (fusigenic peptide/protein), calcium phosphate transfection, electroporation, particle bombardment, direct injection of naked-DNA, diethylaminoethyl (DEAE-dextran transfection) etc. Though the preferred embodiment is the use of plasmid based vectors, the use of other high efficiency viral vectors is not precluded.

The expression vehicles (vectors) of the invention can be engineered by any of a number of techniques known to those of skill in the art. The following is a summary of techniques for construction and transformation of the vectors of the invention.

Genetic Engineering Techniques for Construction and Delivery of Vectors

In a preferred embodiment the expression vehicles or vectors of the invention comprising the expression system also comprise a selectable marker gene to select for transformants as well as a method for selecting those transformants for propagation of the construct in bacteria. Such selectable marker may contain an antibiotic resistance gene, such as those that confer resistance to ampicillin, kanamycin, tetracycline, or streptomycin and the like. These can include genes from prokaryotic or eukaryotic cells such as dihydrofolate reductase or multi-drug resistance I gene, hygromycin B resistance that provide for positive selection. Any type of positive selector marker can be used such as neomycin or ZeoLyn and these types of selectors are generally known in the art. Several procedures for insertion and deletion of genes are known to those of skill in the art and are disclosed. For example in Maniantis, "Molecular Cloning", Cold Spring Harbor Press. See also Post et al., *Cell*, Vol. 24:555–565 (1981). An entire transcription unit must be provided for the selectable marker genes (promoter-gene-polyA) and the genes must be flanked on one end or the other with promoter regulatory region and on the other with transcription termination signal (polyadenylation cite). Any known promoter/transcription termination combination can be used with the selectable marker genes. Examples of such systems include beta-lactase (penicillinase) and lactose promoter systems, (Chang et al., *Nature*, 1977, 198:1056); the Tryptophan (trp) promoter system (Goeddel, et al., *Nucleic Acid Res.*, 1980, 8:4057) and the lambda derived Pl promoter and N-gene ribosome binding site (Shimatake et al., *Nature* 1981, 292:128). Other promoters such as cytomegalovirus promoter or Rous Sarcoma Virus can be used in combination with various ribosome elements such as SV40 poly A. The promoter can be any promoter known in the art including constitutive, (supra) inducible, (tetracycline-controlled transactivator (tTA)-responsive promoter (tet system, Paulus, W. et al., "Self-Contained, Tetracycline-Regulated Retroviral Vector System for Gene Delivery to Mammalian Cells", *J of Virology*, January 1996, Vol. 70, No. 1, pp. 62–67)),or tissue specific, (such as those cited in Costa, et. Al., European journal of Biochemistry, 258 "Transcriptional Regulation Of The Tissue-Type Plasminogen Activator Gene In Human Endothelial Cells: Identification Of Nuclear Factors That Recognize Functional Elements In The Tissue-Type Plasminogen Activator Gene Promoter" pgs, 123–131 (1998); Fleischmann, M., et. Al., FEBS Letters 440 "Cardiac Specific Expression Of The Green Fluorescent Protein During Early Murine Embryonic Development" pgs. 370–376, (1998); Fassati, Ariberto, et. Al., Human Gene Therapy, (9:2459–2468) "Insertion Of Two Independent Enhancers In The Long Terminal Repeat Of A Self Inactivating Vector Results In High-Titer Retroviral Vectors With Tissue Specific Expression" (1998); Valerie, Jerome, et. Al. Human Gene Therapy 9:2653–2659, "Tissue Specific Cell Cycle Regulated Chimeric Transcription Factors For The Targeting Of Gene Expression To Tumor Cells, (1998); Takehito, Igarashi, et. Al., Human Gene Therapy 9:2691–2698, "A Novel Strategy Of Cell Targeting Based On Tissue-Specific Expression Of The Ecotropic Retrovirus Receptor Gene", 1998; Lidberg, Ulf et. al. The Journal of Biological Chemistry 273, No.47, "Transcriptional Regulation Of The Human Carboxyl Ester Lipase Gene In Exocrine Pancreas" 1998; Yu, Geng-Sheng et. Al., The Journal of Biological Chemistry 273 No. 49, "Co-Regulation Of Tissue-Specific Alternative Human Carnitine Palmitoyltransferase IB Gene Promoters By Fatty Acid Enzyme Substrate" (1998)). These types of sequences are well known in the art and are commercially available through several sources, ATCC, Pharmacia, Invitrogen, Stratagene, Promega.

The assay marker gene to be expressed can then be introduced into the vector of the invention. The foreign marker gene DNA typically will comprise a promoterless transcription unit, gene-poly A.

In a most preferred embodiment the vector comprises a specifically engineered multi-cloning site within which several unique restriction sites are created. Restriction enzymes and their cleavage sites are well known to those of skill in the art.

In a preferred embodiment, a packaging cell line is transduced with a viral vector containing the marker nucleotide sequence to form a producer cell line including the viral vector. The producer cells may then be directly administered, whereby the producer cells generate viral particles capable of transducing the recipient cells.

In a preferred embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

Retroviral vectors are useful as agents to mediate retroviral-mediated gene transfer into eukaryotic cells. Retroviral vectors are generally constructed such that the majority of sequences coding for the structural genes of the virus are deleted and replaced by the therapeutic gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

The marker gene may be incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors described in Bender, et al., *J. Virol.* 61:1639–1649 (1987), based on the N2 vector (Armentano, et al., *J. Virol.*, 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point.

In Moloney murine leukemia virus (MoMuLV), 5' to the authentic gag start, an open reading frame exists which permits expression of another glycosylated protein (ppr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., *Biotechniques*, 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragment or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector then is employed to transduce a packaging cell line to form a producer cell line. Examples of packaging cells which may be transfected include, but are not limited to the PE501, PA317, Ψ2, Ψ-AM, PA12, T19-14X, VT-19-17-H2, ΨCRE, ΨCRIP, GP+E-86, GP+envAM12, and DAN cell lines. The vector containing the therapeutic nucleic acid sequence may transduce the packaging cells through any means known in the art. Such means include, but are not limited to, electroporation, the use of liposomes, and $CaPO_4$ precipitation. The producer cells then are administered directly to or adjacent to desired recipient cells.

Integration occurs within the transcribed region of a cellular gene in a fashion that renders the production/accumulation of the marker protein dependent upon transcription initiated at cellular promoters.

Figure 1:
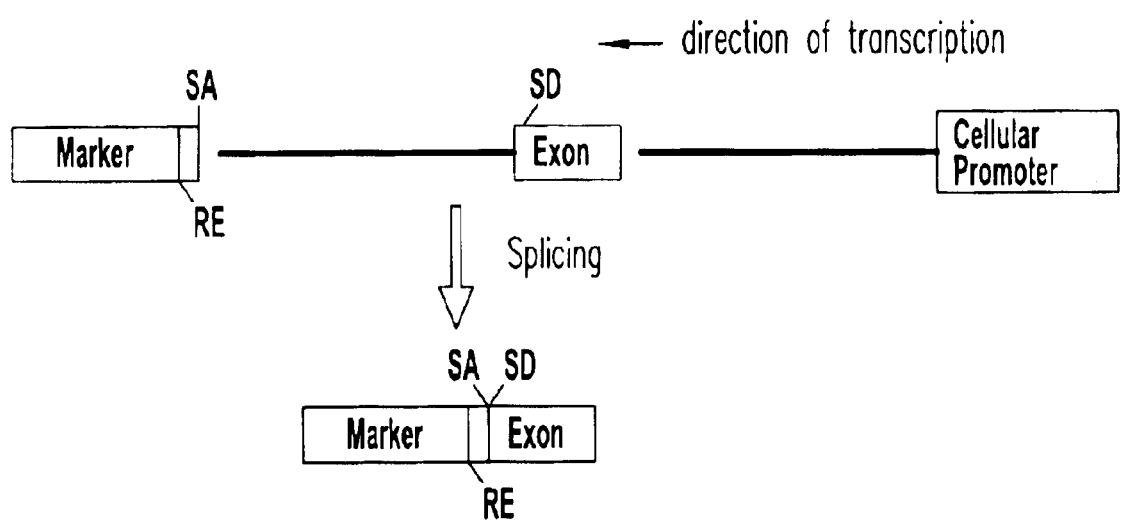
FIG. 1 is a schematic of a vector useful for the invention. In this example, integration of a marker peptide coding sequence can occur either in an intron or exon in split genes encoding protein products (inclusive but not limited e.g. genes without introns that encode proteins such as histones etc., or genes encoding physiologically active RNAs, eg., snRNA, scRNA, spliceosome components etc.). For the sake of clarity, integration into an instron sequence of a cellular gene encoding a protein is shown. Placement of a splicing acceptor (SA) upstream of a marker peptide-encoding sequence results in the synthesis of a mRNA encoding a fusion protein that includes the marker peptide fused to peptide sequences encoded by upstream exons (occurs when the splice donor of the nearest upstream exon (closer to the start of transcription) is reacted to the splice donor present in the integrated marker DNA sequence).

In yet another preferred embodiment the polynucleotide vector may include a "splice acceptor site" so that if the vector integrates in the proper orientation within an intron encoding region of a cellular gene, the marker protein is produced as a fusion product with a portion of whatever cellular protein is encoded by the gene where the insertion event has occurred (Inclusive but not limited to, e.g., inclusion of an internal ribosome entry site (IRES) prior to the start codon of the marker gene ensures it will be expressed whenever RNA from the cellular gene (where integration has occurred) is transported to the cytoplasm in a form that is translatable). (FIG. 1)

Figure 2A:
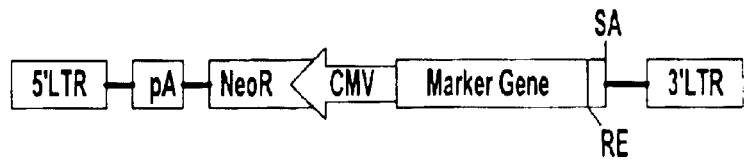
FIGS. 2A–F depict diagrams of several variant constructions of retroviral vectors which perform certain distinct functions for acquiring different types of information in cells. The critical protion is the area located between the 5' and 3' LTR. These expression cassettes would be moved essentially intact between any of the various viruses and/or plasmids that we have mentioned.
Figure 2B:
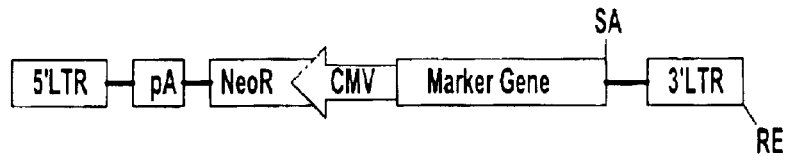
Figure 2C:
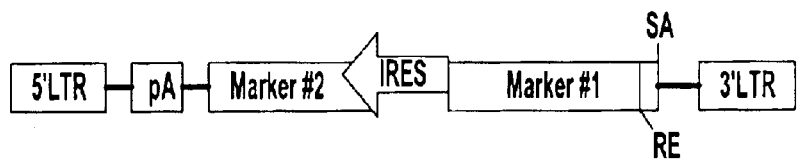
Figure 2D:
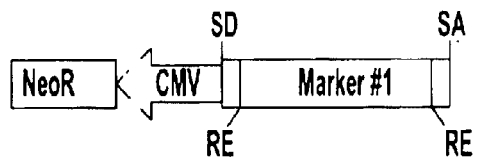
Figure 2E:
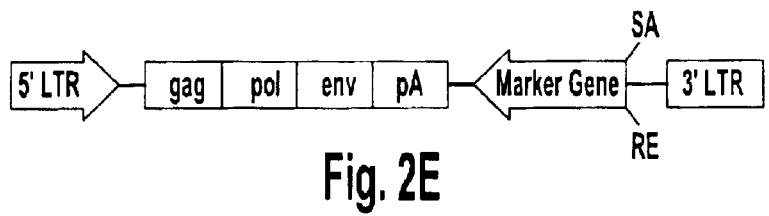
Figure 2F:
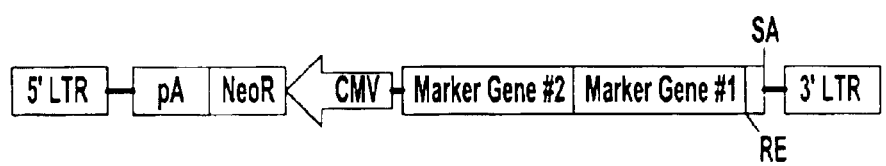
Figure 3:
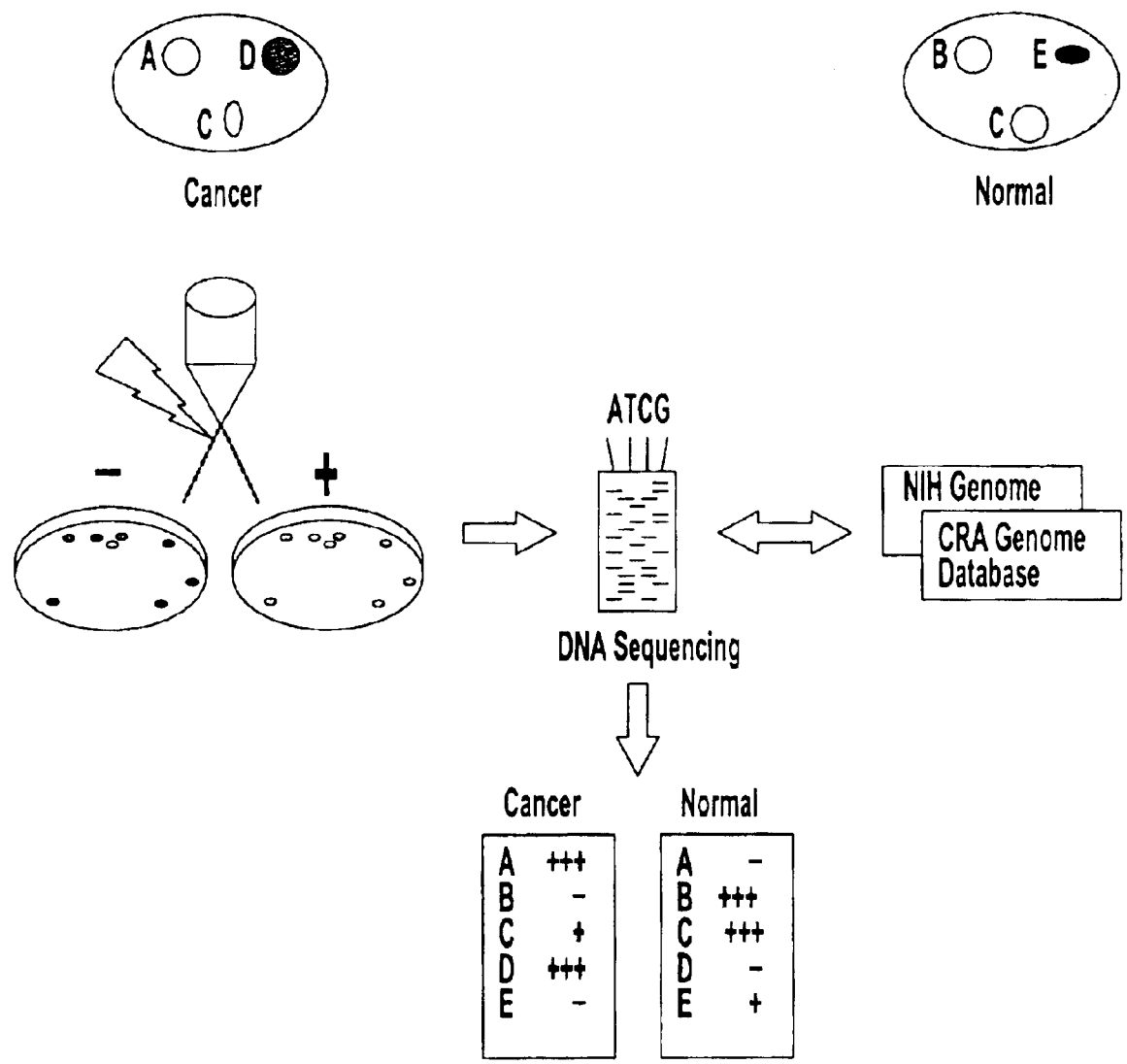
FIG. 3 delivers a rudimentary overview of the process of the invention. The process begins with two different populations of cells to be compared. Each population of cells to be compared will have been marked genetically by a vector containing marker/s-peptides to facilitate detection and determination of relative concentration of marker/s. Left portion of middle panel demonstrates sepration of populations of cells based on relative amount of marker present in the tagged cells. Sequences flanking the vector wil be determined by but not limited to serial analysis of viral integration (SAVI) or sequence tag acquisition and reporting system (STARS) methods. Valid tags will then be compared to public and commercial data bases and annotated into our own data bases.

Similarly, multiple markers may be included such that one marker protein may be expressed as a fusion and a second marker protein may be expressed from an IRES (FIG. 2C) Constructions are also possible to acquire different pieces of information about integration sites, depending upon the positioning of splice acceptor and donor sites.

According to the invention serial gene-trapping vectors for the acquisition of the data needed to assign integration sites to specific genes and to mean marker protein expression levels. Examples of such vectors are shown on FIGS. 2a–2f.

Figure 14:
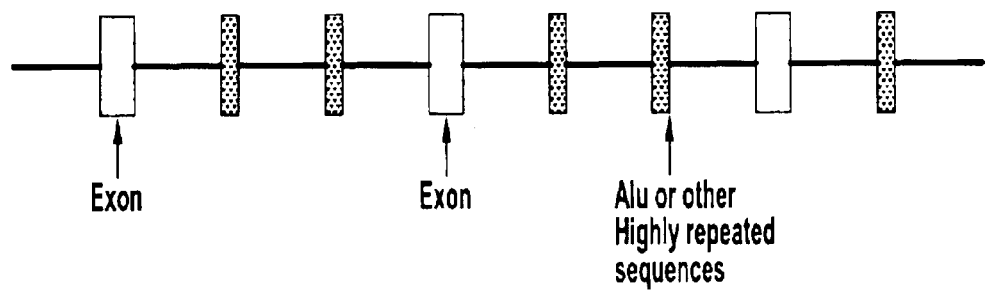
FIG. 14 is a schematic depicting a vector of the invention which utilizes homologous recombination as the integration strategy. The repeat sequences are engineered to flank the assay marker gene and then introduced to the cell.
Figure 14:
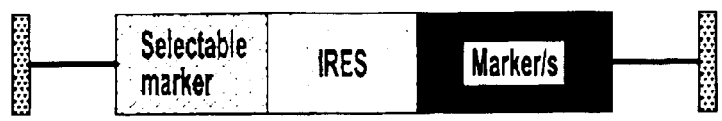
Figure 15:
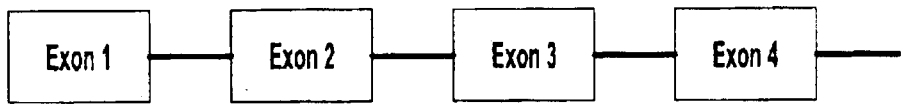
FIG. 15 is a diagram depicting the concept of fram alignment. Only 1 in 3 integrants will be in frame based upon the triplet condon scheme so that only 1 in three integrated vectors will be functional and result in translation of the assay marker.
Figure 15:
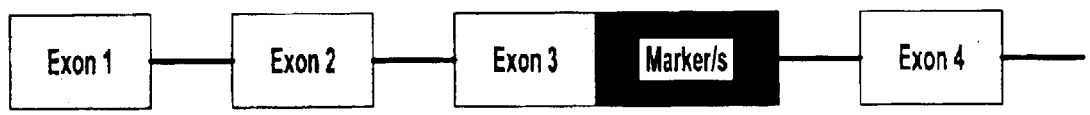
Figure 15:
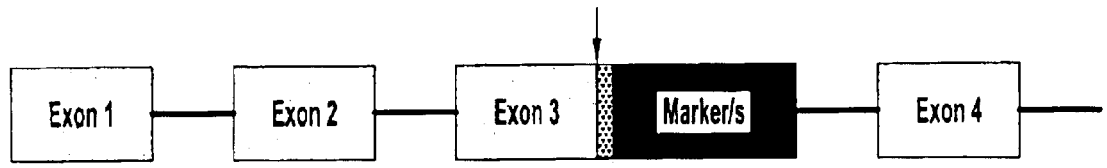
Figure 15:
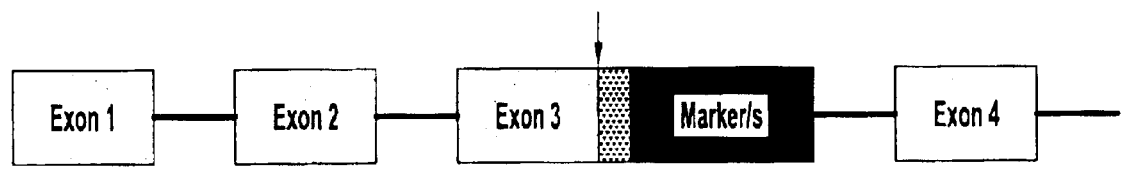

As shown in FIG. 14 the issue of frameshift is also important to consider as only 1 in 3 integrants will be functional. Due to the triplet organization of translation 2 out of 3 integrations will not result in functional assay marker production as they will result in frame shifts which will disrupt the translation of the marker gene despite its integration into an active region of the cellular genome. Thus in yet another preferred embodiment of the invention, a plurality of vectors are constructed which are only one base or two bases different from the start site of the marker gene. This will help to trap some exons which are not in frame after integration of the marker nucleotide.

The production of these various vectors is readily achieved by those skilled in the art. One methodology which may be used for creating the vectors is as follows:

The vectors to be produced as defective retroviruses are transfected into a vector packaging cell lines containing a helper virus (inclusive of, but not limited to, retroviral AMIZ helper virus, or other retroelements (Young, W. B. and C. J. Link, Jr., *Chimeric retroviral helper virus and picornavirus IRES sequence To eliminate DNA methylation for improved retroviral packaging cells* [*In Process Citation*]. J Virol, 2000. 74(11): p. 5242–9) which can prevent the unwanted silencing of helper virus by cellular DNA methylation (Young, W. B., G. L. Lindberg, and C. J. Link, Jr., *DNA methylation of helper virus increases genetic instability of retroviral vector producer cells*. J Virol, 2000. 74(7): p. 3177–87). This AMIZ helper virus-packaging cell line can produce vector titer up to $2 \times 10^7$ CFU (colony formation unit)/ml.

In certain circumstances where the production of retrovirus is limited alternative methods of retroviral production can be performed using a chimeric adenovirus system to produce vector titers up to $5 \times 10^9$ cfu/ml (Ramsey et al., Caplen et al.,).

Sorting of Cells Based Upon Levels of Marker Peptide Expression

Cells which express the marker are then sorted and preferably quantified by their level of expression to generate an expression profile for a particular cell type. Sorting or separation of the cells can be by any method which provides for the separation and preferably quantification based upon expression of the marker sequence. This could be by fluorescence activation sorting, mechanical sorting, charge or density etc.

A preferred method of sorting includes the use of flow cytometry. Flow cytometry seeks to utilize complex integration of optic, fluidic, and electronic components to develop fluorescence activated cell sorters (FACS) capable of rapid interrogation of cells containing useful fluorescent marker/s in real time.

Marker which may be sorted by this method include cell surface displayed protein; lipid, lipoprotein, glycolipid, and glycoprotein targets that can be tagged with specific fluorescent compounds using labeled antibodies, direct chemical linkage and/or combination of direct and indirect tagging.

One alternative embodiment includes the use of high-sensitivity/high-density plate readers to detect chemiluminescent signals (range $1 \times 10^{-18}$ M to $1 \times 10^{-21}$ M) or with concomitant decreased sensitivity conventional plate reader technology can be used to measure absorbance of enzyme based chromophores. A method for sorting cells with similar speed to that of conventional FACS may be employed where the electrical charging plates are replaced with high performance electromagnets that allow magnetic based separation. Alternatively, confocal microscopy will allow increased sensitivity but with significant reduction in through put.

In a preferred embodiment the assay marker peptide is a naturally fluorescent protein fusion product that includes but is not limited to humanized renilla reniformis green fluorescent protein (hrGFP) with FACS separation. Examples of uncloned GFP molecules useful for practice of the invention have been sited in Cormier, M. J., Hori, K., and Anderson, J. M. (1974) Bioluminescence in Coelenterates. *Biochim. Biophys. Acta* 346:137–164. In cases where fluorescent signal of the tagged fusion proteins are of insufficient magnitude to be useful the cells may be probed again with enzyme labeled fluorescence.

In a further embodiment ELISA and Western blotting may be used to establish correlation curves that increase the accuracy of the protein estimations. Alternatively, RIA and/or immunoprecipitations can be used to establish standard correlation curves of target protein content. Preferably a consistent standard and calibrator set of beads will be developed with a known number of molecules of fluorescent protein bound per bead. These standard beads will allow correlation of fluorescent intensity to molecules equivalent soluble fluorescence.

In another optional embodiment the expression construct includes a polynucleotide with a negative or positive selection protein for enrichment of the population prior to sorting. Use of the negative or positive selection will remove from the population all cells with no integration of the polynucleotide, for example via antibiotic resistance. This provides for enriched populations of target cells to overcome any relative inefficiency of the gene trapping of genomic control elements. Enrichment of gene trapped cells will include the use of drug selection (ex. neo$^r$, puro$^r$, hygro$^r$, zeo$^r$, HAT$^r$ etc.), affinity separations to include but not limited to {Ab/Ag or Ab/hapten, biotin/streptavidin, glutathione S-transferase (GST) fusion proteins, Polyhistamine fusion proteins (Invitrogen), calmodulin-binding peptide tag (Stratagene), c-myc epitope tag (peptide seq. EQKLISEEDL) (Stratagene), FLAG epitope tag (peptide seq. DYKDDDDK) (Stratagene), V5 epitope (Stratagene), the Linx™ technology {phenyldiboronic acid [PDBA] and salicylhydroxamic acid [SHA]} (Invitrogen), adhesion, blocking of adhesion, chemotaxis, block of chemotaxis etc.}, and/or enrichment by FACS using fluorescent Ab, fluorescent Ag, fluorescent substrates or non-fluorescent substrates that become fluorescent after enzymatic cleavage/activation (A complete listing of common fluorescent probes used for our applications can be found in references: Shapiro, H. M., *Practical Flow Cytometry*, Third Edition, Wiley-Liss (1994), Robinson, J. P., *Handbook of Flow Cytometry Methods*, Wiley-Liss (1993); Ormerod, M. G., *Flow Cytometry: A Practical Approach*, Second Edition, IRL Press (1994); Robinson, J. P., *Current Protocols in Cytometry*, John Wiley & Sons (2000).

Alternatively, some applications may use depletion of cells that demonstrate very high levels of protein expression to allow finer fractionation of cells demonstrating lower expression of the marker peptide (e.g., negative selection {including but not limited to HSV tk/GCV,}. This negative selection can be applied before or after a positive section process.

According to the invention populations of marker peptide (gene trapping) cells will be sorted by FACS into various levels of expression based on the distribution of number of cells and relative fluorescent intensity. The cells which may be either viable or fixed in preservatives (e.g., paraformaldehyde) will then be sorted into groups based on mean fluorescence intensity. The process is equally efficient with dead fixed and non fixed cell or cells that have been permeabilized and probed with fluorescently labeled Ab or enzyme labeled fluorescent probes to increase sensitivity. Cytometry 23, 46 (1996); J Histochem Cytochem 43, 77 (1995).

Once the sorting process is completed DNA, RNA, and/or total protein may be extracted and subjected to down stream amplification and/or analysis (although live cells could be returned to culture for further amplification if it is deemed necessary to do so).

Sequence Tag Acquisition and Reporting

Once the protein levels are separated out the protein is associated with a particular genomic loci. This is accomplished by defining the flanking sequences around the integration site of the marker peptide expressing retroviral vectors (e.g,.molecular DNA bar code) after the cells have been interrogated by FACS and a relative level of protein expression derived from the relative fluorescence intensities of the cells.

Fractionation of the entire population of cells (with measurable levels of marker protein expression) into subpopulations of cells (each subpopulation comprised of cells with similar levels of marker protein expression) is followed by analysis of integration sites within the cells of a subpopulation. As integration sites are identified (and correlated with a genetic locus) they are assigned the mean subpopulation marker protein level as a measure of relative expression. When complete, all analyzed integration sites/genes will have a relative level of protein expression assigned to them.

Figure 16:
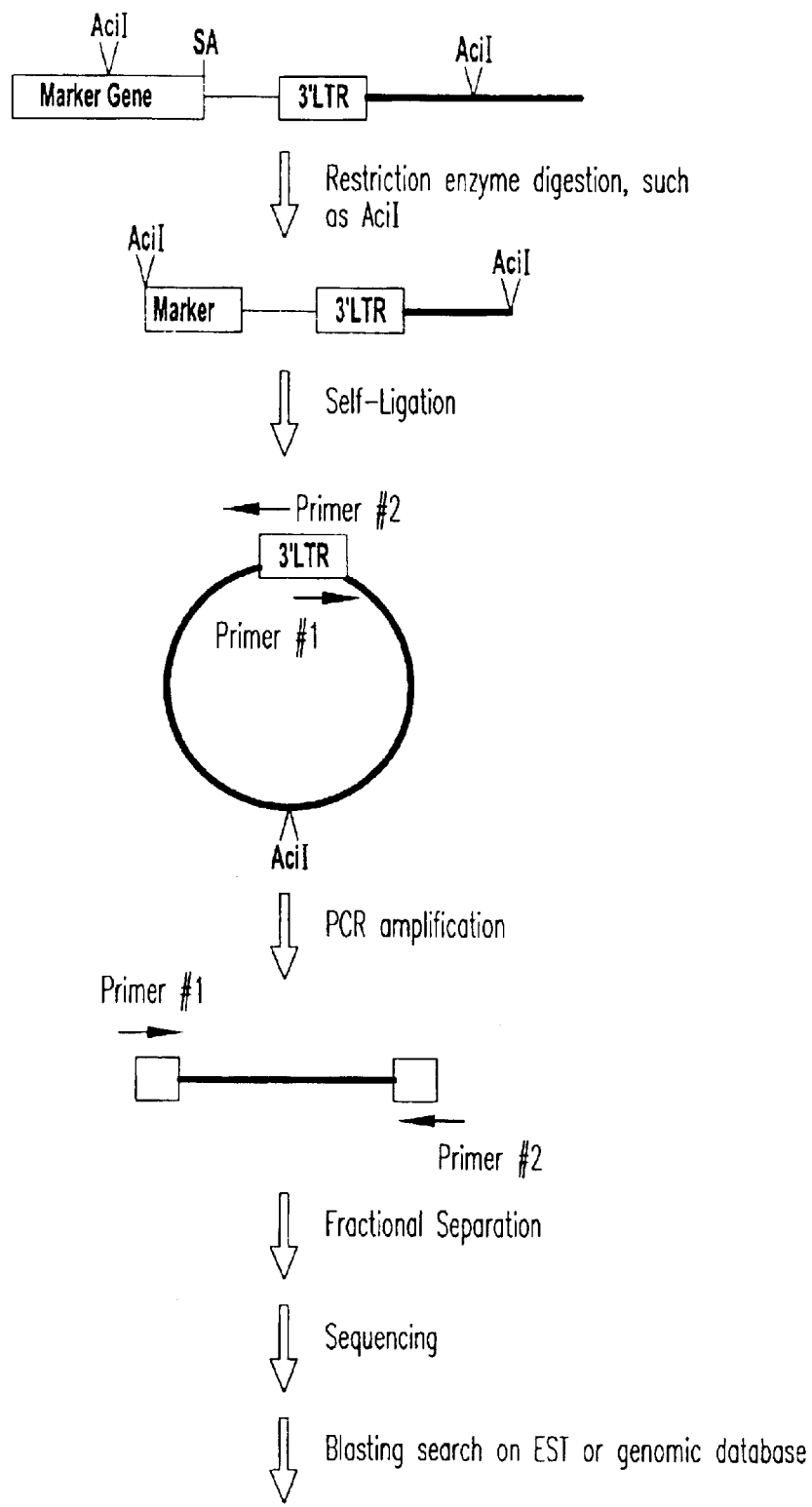
FIG. 16 is a schematic depicting the STARS process. A method of cleaving said cellular DNA such that inserted DNA (with sequence known to the operator) is cleaved once and flanking cellular DNA of unknown sequence is cleaved again in the regions contiguous to the inserted piece of DNA. Clearage of the DNA occurs in a fashion generating ends that permit the circularization of DNA fragment sproducing a molecule with the sequence known to the operator flanking both sides, and continuous with a variable length of cellular DNA of unknown sequence. The region containing the unknown DNA is then amplified and sequenced.

For the purpose of this example, we describe a method for the acquisition of the data need to assign integration sites to specific genes and to mean marker protein expression levels. It is inclusive of, but not limited to, the examples listed below:

A. The method of Sequence Tag Acquisition and Reporting System (STARS) (FIG. 16):

Recovery of genetic material from the cells to be analyzed, in this example cellular DNA(inclusive of, but not limited to, cellular DNA since complementary DNA derived from cellular RNA (cDNA)may be used), the composition of which is partially known to the operator by virtue of the inclusion of the sequences encoding the marker peptide. The genetic locus containing the inserted sequence (or producing the RNA containing inserted marker gene sequences) is known as the "tagged gene."

A method of cleaving said cellular DNA such that inserted DNA (with sequence known to the operator) is cleaved once and flanking cellular DNA of unknown sequence is cleaved again in the regions contiguous to the inserted piece of DNA. Cleavage of the DNA occurs in a fashion generating ends that permit the circularization of DNA fragments producing a molecule with the sequence known to the operator flanking both sides, and continuous with, a variable length of cellular DNA of unknown sequence.

Primers comprised of sequences drawn from that sequence known to the operator (part of the expression vector) are used in the amplification of unknown sequences, in this example by polymerase chain reaction (inclusive of, but not limited to, since other means of amplifying sequences as RNA molecules could be used). These primers are selected to bind to the circularized product described previously, in the regions of DNA whose sequence is known to the operator, and prime the synthesis of DNA proceeding in opposing directions causing amplification of the DNA segment of unknown sequence. The product of this reaction will thus contain two terminal segments of DNA sequence known to the operator (as described supra, and an internal DNA segment of unknown sequence. This amplified DNA molecule is known as the captured amplimer.

The captured amplimer is analyzed for the nucleotide composition of the region whose sequence is unknown to the operator. This may be achieved by any of several methods known to those skilled in the art. Importantly for the invention, the sequence composition is not required to be determined in its entirety, rather a segment adequate to allow identification of its origins by comparison to a sequence database of known composition, e.g. GENBANK.

The region of the captured amplimer that provides the sequence for comparison is known as the captured sequence. Comparison of the captured sequence to a database can be performed by any of several means known to operators skilled in the art, in this example using BLAST analysis. That portion of the captured sequence that can be matched to the sequence of genetic loci contained in the established database is referred to as the sequence tag.

The sequence tag, once acquired and annotated with the corresponding genetic locus information and assigned a mean marker protein expression value, then may be used to correlate with a reference cell type. This identifies a potential drug target or a diagnostic indicator of a disease state or other diagnosable difference between the two cell types.

B. Serial Analysis of Viral Integration (SAVI)

Figure 17A:
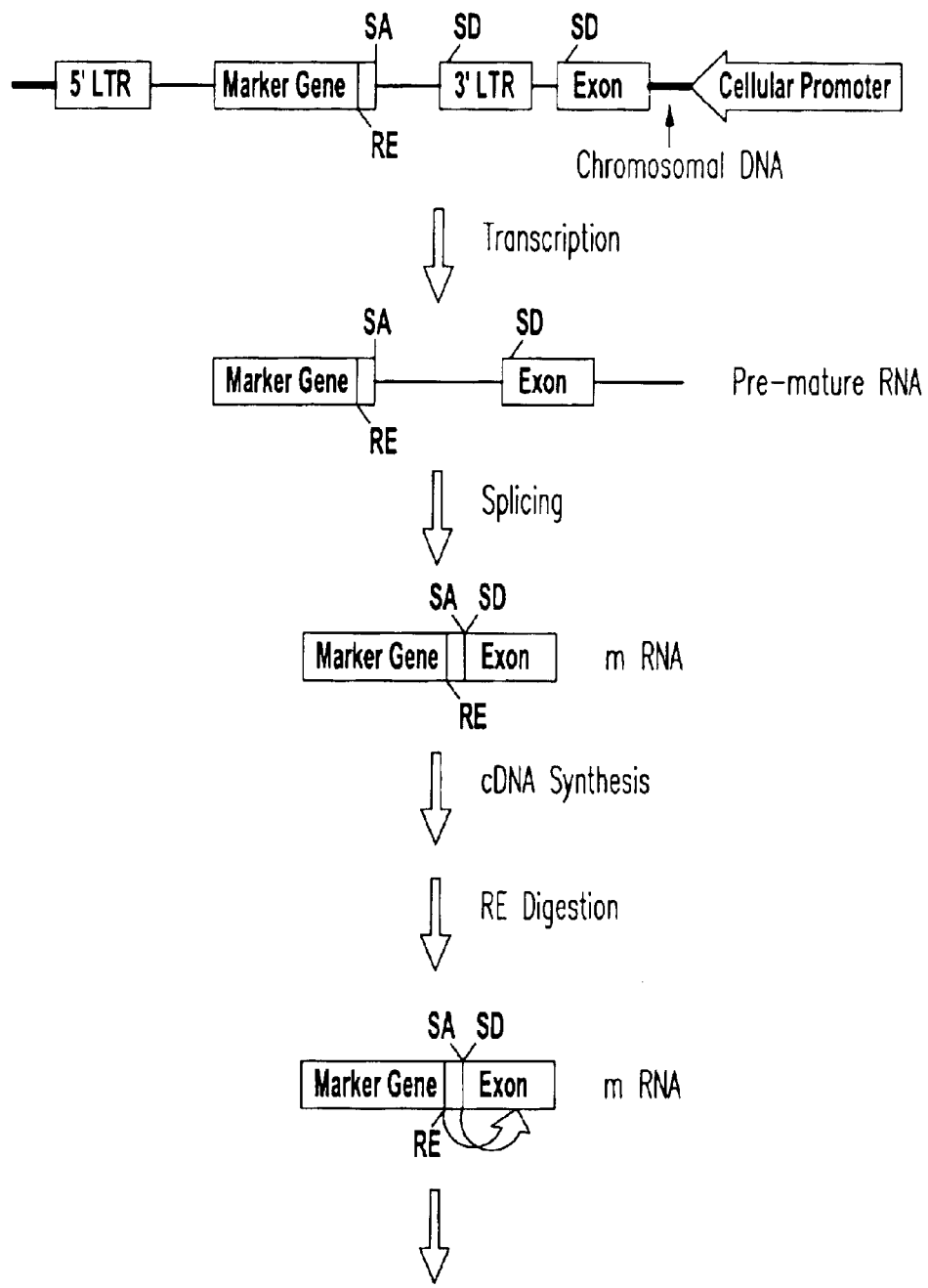
FIGS. 17A and B depict the SAVI process. Integration of a marker gene can occur either in a intron or exon. Adjacent a splicing acceptor (SA) in front of a marker gene can therefore result in a fusion protein for marker gene expression after the integrated gene exon region is spliced into the SA signal of the marker gene. However, to sequence the exon region of this integrated gene to release the identity becomes a problem.
Figure 17B:
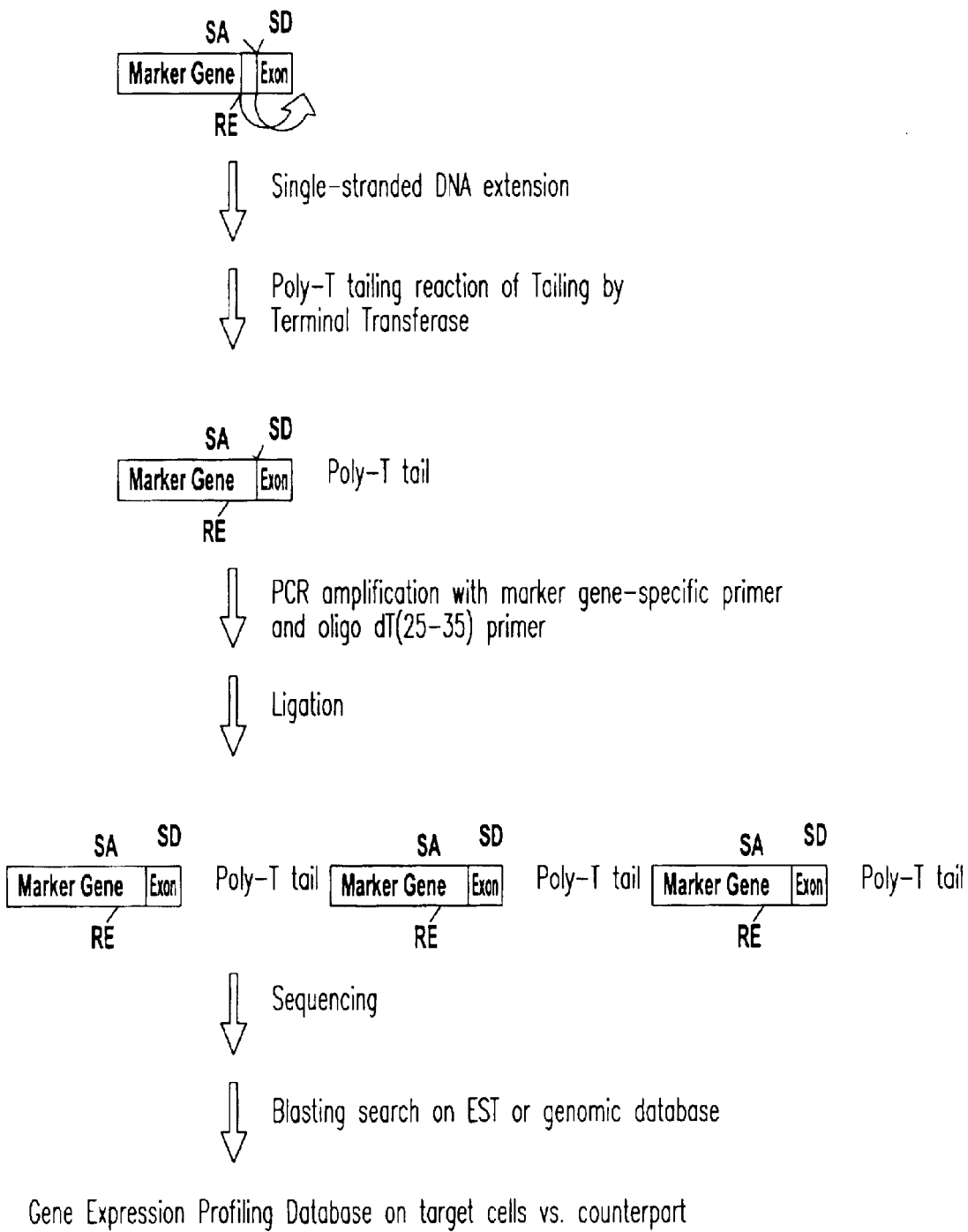

For correlating the protein expression data to a loci includes SAVI (FIG. 17). The method of serial analysis of viral integration (SAVI) is comprised of: Recovery of genetic material from the cells to be analyzed, in this example complementary DNA to cellular mRNA (inclusive but not limited to, as a cellular DNA equivalent derived from nuclear RNA may be used), the composition of which is partially known to the operator by virtue of the inclusion of the sequences encoding the marker peptide. The genetic locus containing the inserted sequence (or producing the RNA containing inserted marker gene sequences) is known as the "tagged gene".

For this method a restriction enzyme is used which cuts at a known site within one end of the expression construct. Thus the cDNA is cleaved such that inserted marker DNA (with sequence known to the operator) is recognized and flanking cDNA (of cellular origin) of unknown sequence is cleaved by an enzyme at a site a fixed distance from the sequence known to the operator and recognized by the restriction enzyme (within the regions contiguous to the inserted piece of DNA). The cleavage of the DNA occurs in a fashion generating ends that permit the ligation of multiple lengths of DNA fragments all from an identical starting point producing a concatenated molecule composed of units comprised of sequence known to the operator continuous with a short length of cDNA (or cellular DNA) of unknown sequence. Each unit is known as a captured integration site. Concatamers composed of multiple units are referred to as serial integration site polymers.

Serial integration site polymers are sequenced by any of several methods known to those skilled in the art. For example they may be cloned into appropriate bacterial plasmid hosts such as pCR2.1 (Invitrogen), amplified, and plasmid DNA isolated and sequenced by any of several methods including PCR chain termination, the methods of Sanger, or those of Maxam and Gilbert.

The sequence obtained is analyzed by segmentation into defined lengths (established by the specificities of the enzyme used earlier and is known as a "captured viral integration sequence." Comparison of the captured sequence to the database can be performed by any of several means known to operators skilled in the art, in this example using BLAST analysis. That portion of the captured sequence that can be matched to the sequence of genetic loci contained in the established database is referred to as the "captured SAVI sequence tag."

The "captured SAVI sequence tag" is then annotated with the genetic locus and the mean marker protein expression value and is denoted the "SAVI sequence tag." This information can be used as described earlier.

The application of these technologies yield several important types of information. First, the ability to generate "captured amplimers" (from both genomic DNA and from cDNA) containing sequences of host cell DNA adjacent to the integrated virus provides data that may determine whether the carcinogenic effects of the virus are due to insertional mutagenesis, or more likely, to the expression of viral genes. This information may be particularly relevant in establishing drug regimens to block expression of the viral genes or to block specific changes in cellular gene expression resulting from site-specific HPV integration.

Perhaps more importantly, the ability to quantify the frequencies at which particular sites of viral integration have occurred can provide information on the clonality of analyzed lesions, potentially even from samples such as Pap smears. This is important because the presence of clonal populations of cells expressing the integrated viral transforming genes should correlate with the development of cancer in humans (as is seen in rodent models).

Similarly, bronchoalveolar carcinoma in humans shows characteristics strikingly similar to tumors induced in sheep by a viral pathogen (Jaagsiekte virus) although no etiologic agent has yet been identified. The application of the methods of the invention in combination with preparation of EST libraries from bronchoalveolar carcinomas and surrounding normal tissues from patients with this disease could provide information on the causative agent in humans providing diagnostic/prognostic markers that can be exploited. Besides these clinical applications, these data acquisition and reporting systems can also be used to study the mechanism of alternative splicing and the gene expressions regulated in alternative splicing manner. The transcriptional levels of genes can also be digitalized and represented by the frequency of genes being captured. The product of these captured gene tags will be used as probes to hybridize a DNA microarry for data validation.

Bioinformatics

In an optimal embodiment the sequence tags and their associated fluorescence/mRNA levels will be used as input. This data will be analyzed concomitantly with publicly and privately available data.

The resultant data can be imported into a proprietary database, or mined directly for quick comparison and pattern matching. This activity will result in a wide variety of information including but not limited to pharmacogenetic targets, pathway and metabolic analysis, comparison of protein expression between and within species, organisms, and cell states.

For the purpose of this application, the term genetic locus is used to specify a particular location within the context of the genome and does not imply a complete transcription or regulatory unit, instead referring to a specific sequence which may comprise all or part of such functional units or sites.

For the purpose of this application, marker protein concentration refers to the concentration of specific individual protein configurations which result from phosphorylation, acetylation or other structural modifications which affect functional state (e.g., dimerization vs monomer) in addition to any assumed unmodified peptide arising from the translation of a mRNA.

Data Aggregation Process:

The preferred embodiment of the aggregation process consists of four steps. These steps are: 1) Matching the tag against its respective protein sequence, 2) Associating a concentration or count level with the tag that is derived from data measured in the FACS module, 3) Combining all of the available tag protein level data for each genetic locus to arrive at some composite value for that respective genetic locus, 4) Creating tables that represent the information for each tag and the composite information for each genetic locus. Steps one and two are order independent, meaning that step two can occur before step one without any problems for the process.

Implementation of step one begins with the receipt of sequence tags (a variable length DNA sequence that will usually be between 16–25 bases) and associated marker protein concentration data (in this example, but not limited to FACS-derived data). Each tag is compared with a database that contains sequence information of the proteins in the organism of interest. Many methods of making this comparison are possible. Potential methods include but are not limited to: hashing algorithms, dynamic programming alignment algorithms (such as Smith-Waterman and Needleman-Wunsch alignment algorithms), suffix trees and arrays, inverted lists, and combined approaches (such as BLAST (combination of hashing and dynamic programming)) as well as any other string alignment algorithm.

The database can consist of annotated or unannotated genomic sequences that find expression in cells as RNA (independent of their translation into protein, e.g., snRNA, scRNAs, RNAs with catalytic activities, etc.), cDNA libraries, EST libraries, protein sequence libraries (including DNA sequences (with or without intronic or exonic sequences) and amino-acid sequences (including primary, secondary and/or tertiary structure information)). Examples of such databases would include the publicly available EST and genomic databases. The end result of the matching step is that every tag becomes associated with a genetic unit (including subdivisions thereof such as specific intron or exon within a transcription unit) or becomes marked as an unknown so that it can be run again as more information about the proteome/transcript becomes known.

In step two each tag has data associated with it that can be used to derive a quantitative value/s (marker protein concentration) for each individual tag. The derivation of this quantitative value consists of applying a formula (derived earlier in the process) to the raw fluorescence level.

Step three consists of taking the individual tag marker protein concentration levels for each individual genetic locus and combining them to create composite value/s for the genetic locus and those closely related loci (e.g., other introns or exons) within a transcription unit. (This value may have various statistical data associated with it including, but not limited to, measures of central tendency, variance.) The derived data represents a statistical profile of the protein concentration dependent upon the properties of the cells being surveyed (e.g., marker protein stability, transport, cellular autofluoresence, etc.). The derivation process will be optimized for each organism. This optimization may incorporate a wide variety of methods including, but not limited to, comparison of the individual tag's marker protein concentration (in this example FACS-derived but not limited to, e.g. ferrous conjugate and electromagnetically fractionated) with protein levels as measured by other empirical methods (e.g., ELISA, NMR, 2-D gel electrophoresis) and the use of general biological knowledge about protein structure and regulation. These different methods will allow the determination of the accuracy of tags from different regions of proteins on a proteome wide level as well as a more detailed level (for example protein families, superfamilies, proteins with any significant homology, and individual proteins). For those transcription units that produce no translation products, marker protein concentration values of zero can be assigned. Although these genetic loci will not be useful for the determination of direct protein/genetic locus correlation, integrative studies can determine whether expression of these transcripts correlate with changes in the pattern of expression at other loci and/or participate in more global regulatory phenomena such alterations in the selection of alternative splicing sites, polyadenylation sites, cytoplasmic transport/stability properties, ribosome binding and other translational events, etc.)

Step four consists of placing all of the input and consequently derived information into tables that are suitable for further detailed analysis or loading into a database. The resulting tables will be relational to support the use of analysis tools including, but not limited to, those found in standard OLAP applications, industrial engineering, operations research, artificial intelligence, forecasting techniques, clustering, genetic network inference and pathway analysis. Examples of such data analysis techniques include but are not limited to phylogenetic tree construction, k-means clustering, expectation maximization, self-organizing maps, support vector machines, various public-domain algorithms, as well as mathematical/statistical models like Boolean networks, applications of differential equations, and stochastic and hybrid petri nets.

EXAMPLE 1

Results and Descriptions of Vectors

Figure 4A:
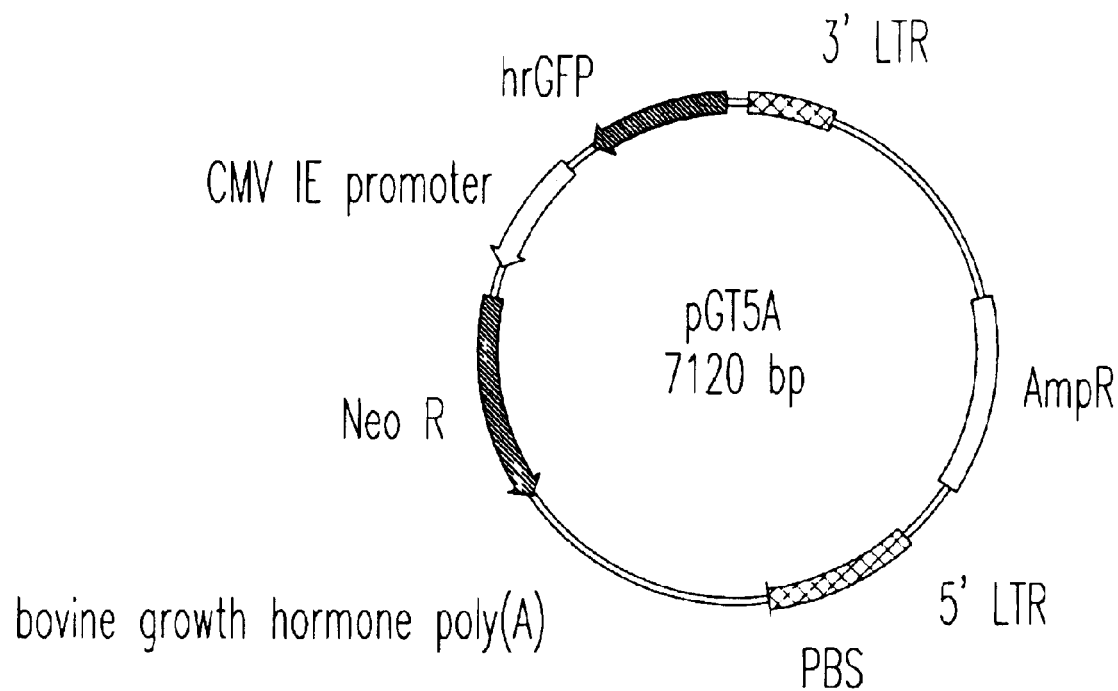
FIGS. 4A and B depict a gene trap vector, pGT5A with a humanized rellina fluorescence protein (hrGFP) as an assay marker, or reporter gene.
Figure 4B:
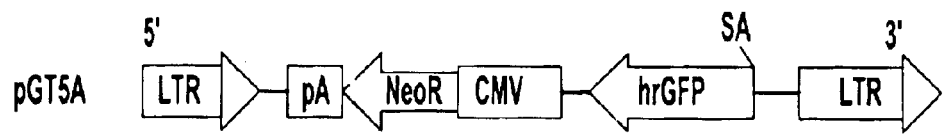
FIG. 4B is a schematic of the order of genes in pGT5A vector.
Figure 5A:
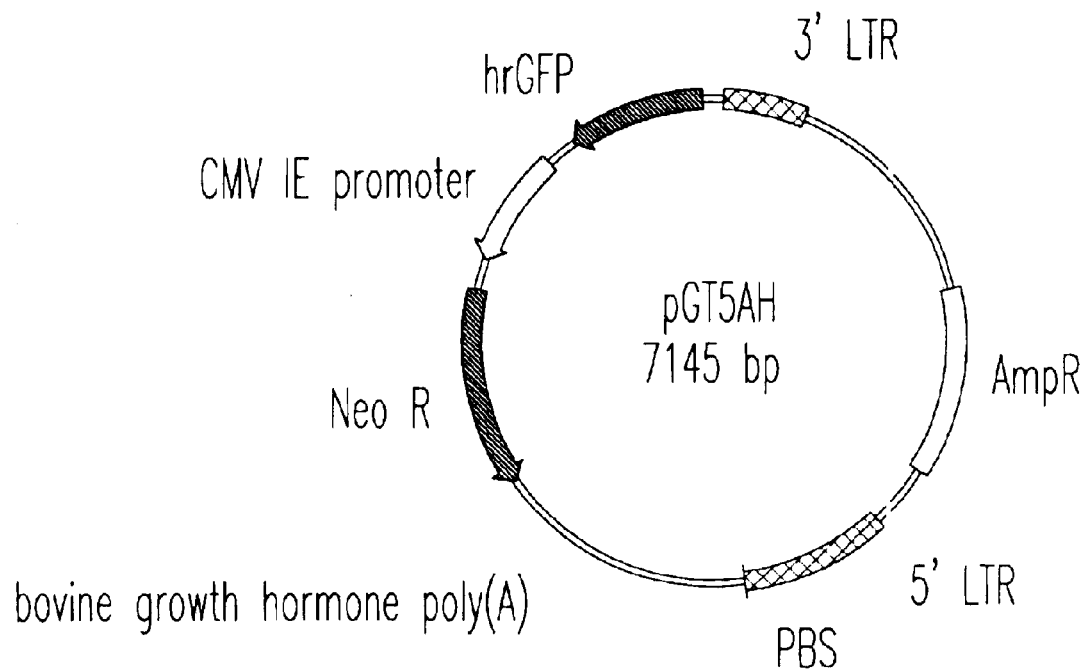
FIGS. 5A and B depict a vector, pGT5AH with a humanized rellina fluorescence protein (hrGFP) as an assay marker, or reporter gene.
Figure 5B:
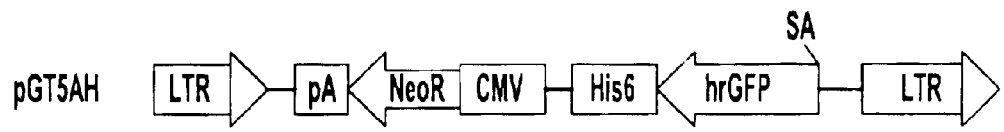
FIG. 5B is a schematic of the order of genes in pGT5AH vector.
Figure 6A:
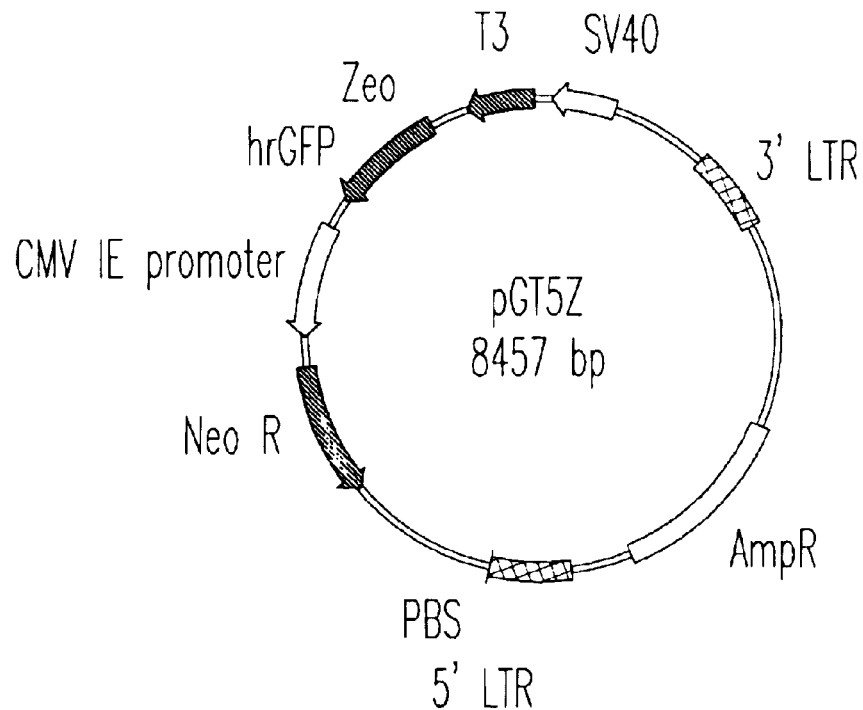
FIGS. 6A and B depict pGT5Z with ahumanized rellina fluorescence protein (hrGFP)) as an assay marker, or reporter gene and Zeocin-resistance gene (ZeoR).
Figure 6B:
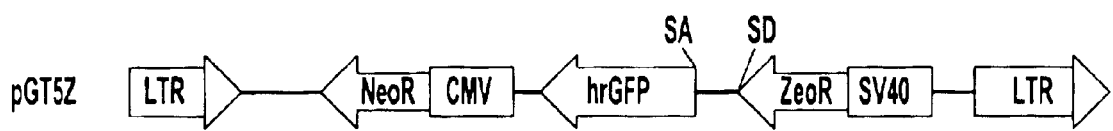
FIG. 6B is a schematic of the order of genes in pGT5Z vector.

A polynucleotide construct (Gene Trap (GT) vector) was constructed with a splicing acceptor (SA) signal of human γ-globin intron #2 in front of humanized rellina green fluorescence protein (hrGFP) to ensure that the hrGFP can be spliced into the exons of trapped genes (FIGS. 4–6). This SA-hrGFP then was inserted into a retroviral vector in an anti-sense orientation to avoid the interference of the transcription function of 5' LTR, further more, the 3' LTR of this retroviral vector has been altered with a deletion of U3 region. The duplication of this deletion in 3' LTR into 5' LTR during reverse transcription disables the 5' LTR promoter function. Therefore, this vector becomes a self-inactivation (SIN) vector. For titer analysis and, to ensure the existence of GT vector in retrovirally transduced (infected) cells, a G418 selection marker gene (NeoR) driven by human cytomegalovirus intermediate-early (CMV IE) promoter was inserted in the vector after hrGFP followed by a bovine growth hormone polyadenylation signal (BGH pA). These genes and functional signals were constructed in reverse orientation to LTRs. The gene expression of hrGFP can only occur after this vector is integrated into the downstream of a cellular promoter.

Figure 7A:
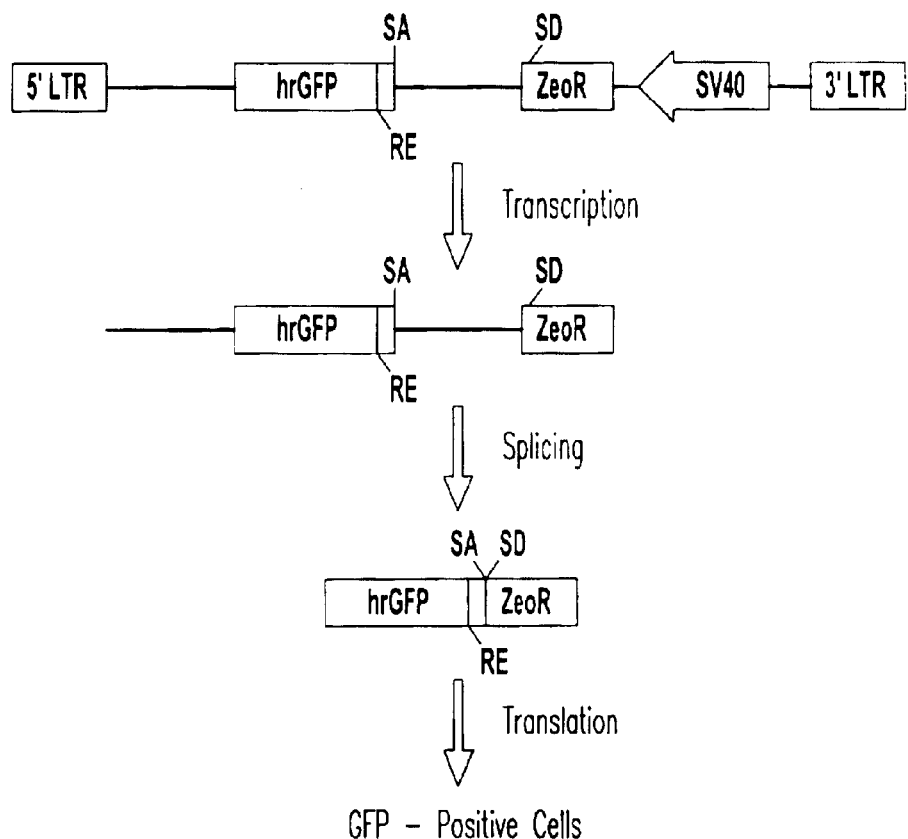
FIGS. 7A and B depict a demonstration of the splicing function and fusion hrGFP protein expressed by pGT5A vector.
Figure 7B:
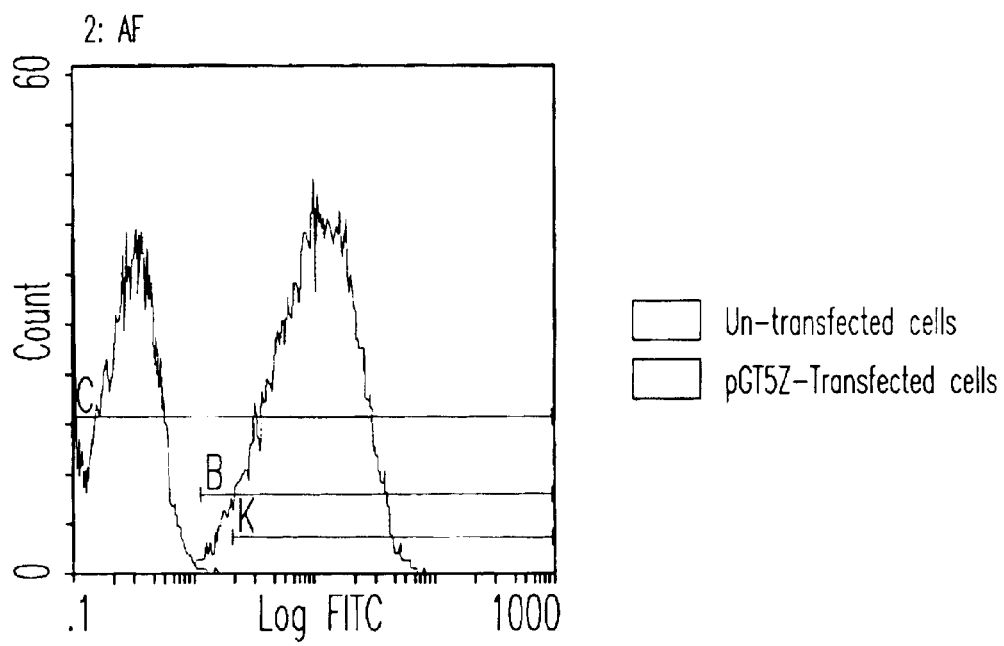
FIG. 7B demonstrates that pGT5Z-transfected cells after Zeocin selection showed siginificant Zeocin-hrGFP fusion protein expression by FACS analysis.
Figure 8A:
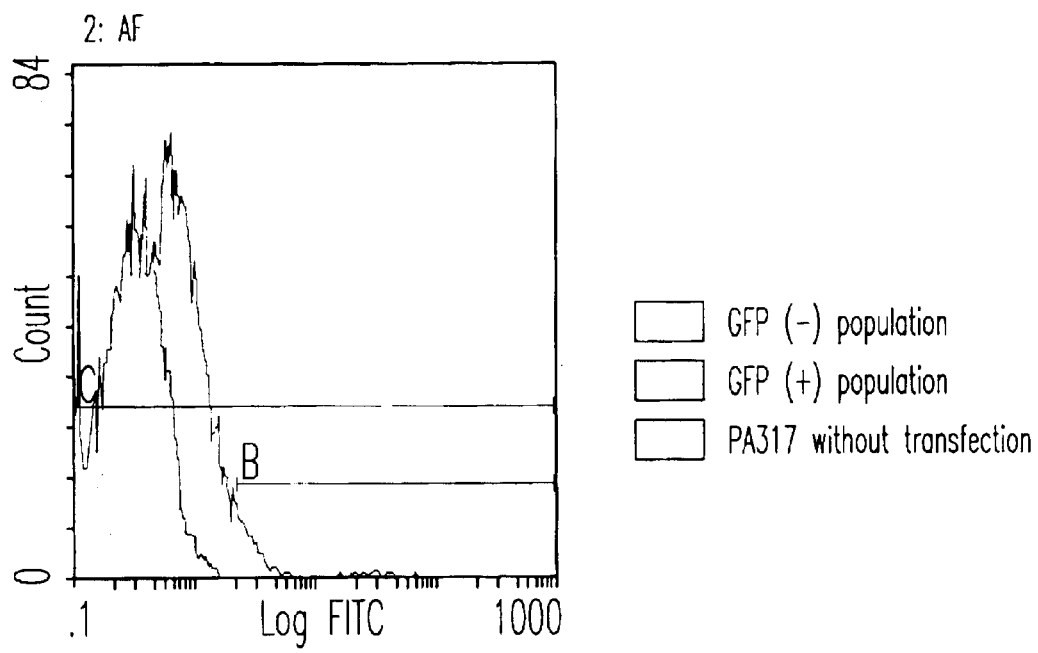
FIGS. 8A and B depict a gene trapping of PGT5A-transfected PA317 cells.
Figure 8B:
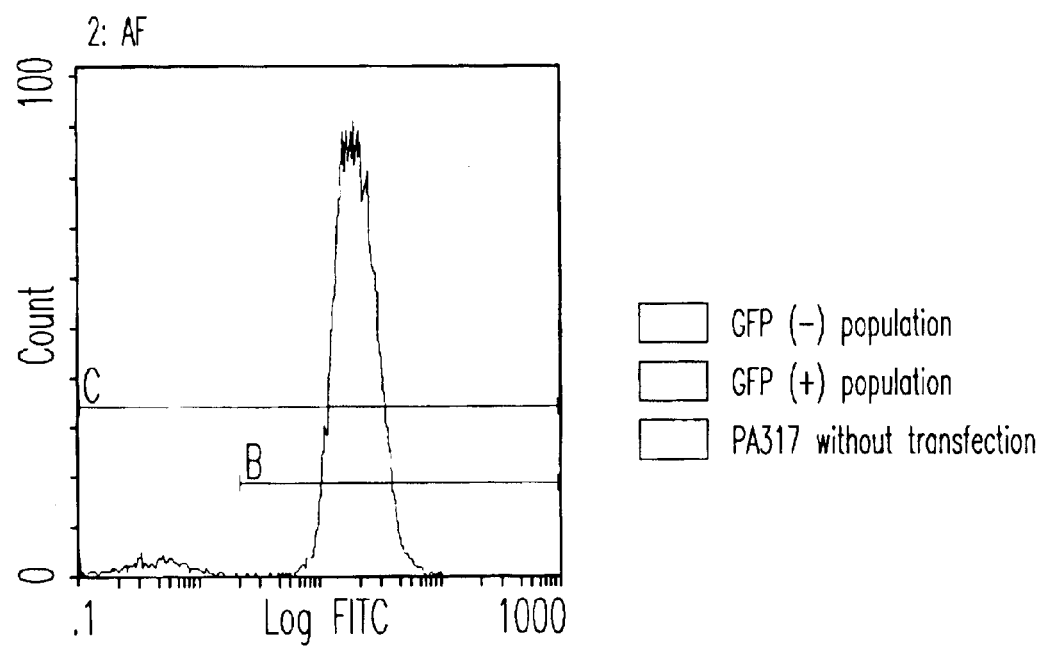
FIG. 8B demonstrates that sorting of the hrGFP-positive cell population in FIG. 8A by FACS cell sorter, hrGFP-positive population was enriched to 95% after 2 weeks of cell culture.
Figure 9:
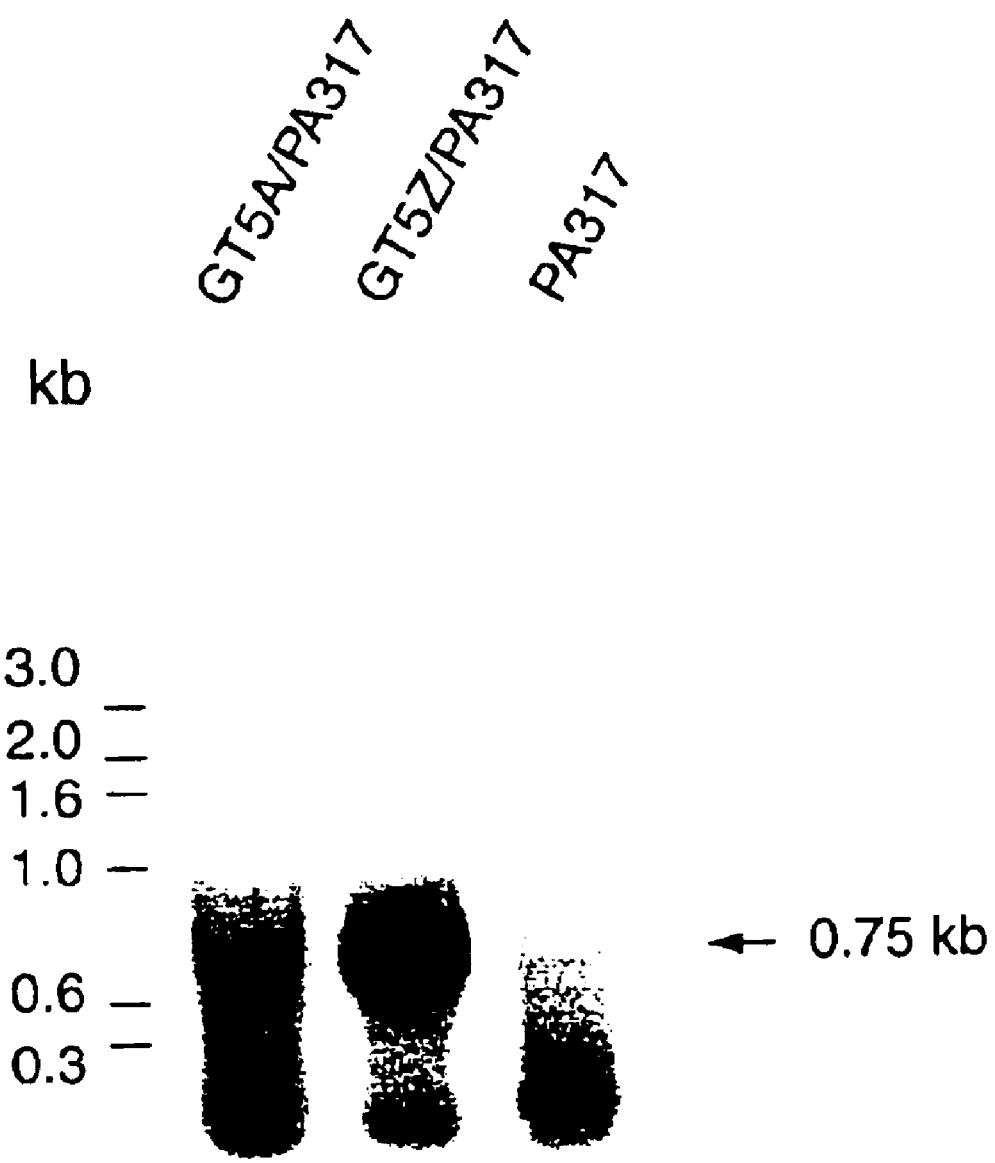
FIG. 9 is a depiction of gene expression of hrGFP in gene trapped PA317 cells. RT-PCR was performed on total RNA extracted from sorted cells in FIG. 7 and FIG. 8, and PCR product was electrophoresed in 2% agarose gel. The whole length of hrGFP transcripts driven by trapped cellular promoter (GT5A/PA317) were amplified by hrGFP specific primers after cDNA synthesis as indicated with an arrow. Transcripts from GT5Z in PA317 (GT5Z/PA317) and PA317 without vector (PA317) were used as a positive and negative control.
Figure 10A:
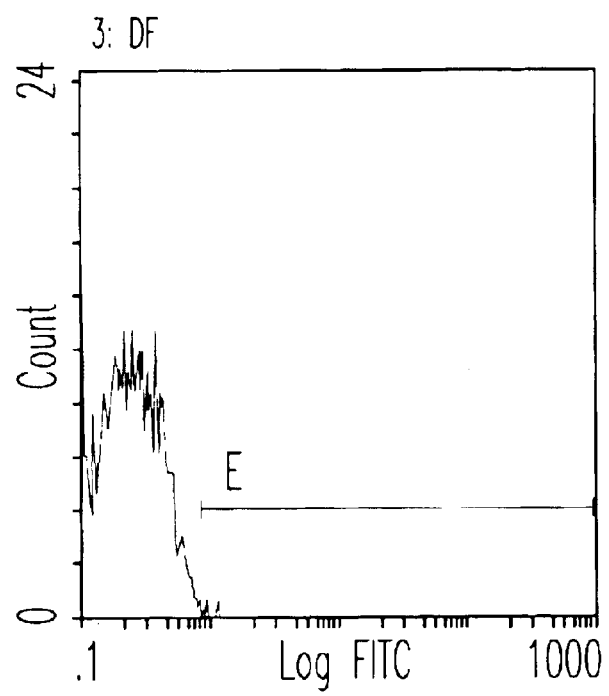
FIGS. 10A and B depict gene trapping of GT5A vector in human lung cancer cells. A549, after viral transduction.
Figure 10B:
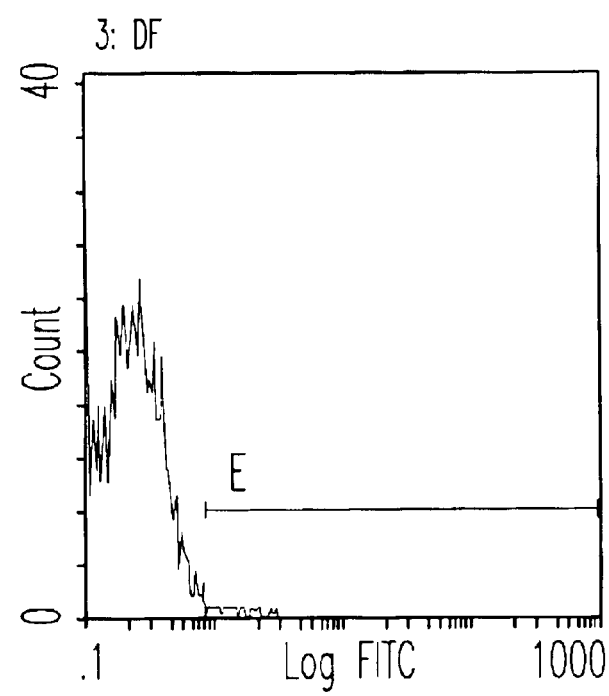
FIG. 10B demonstrates that A549 cells with GT5A-transduction analyzed by FACS showed the hrGFP-positive population is 1.68% after gene trapping

We have been able to show successful gene trapping with our GT vectors in murine fibroblasts, NIH3T3 (FIGS. 11 and 12) and PA317 cells (FIG. 8), human lung cancer cells (FIG. 10). Fluorescence-activated cell sorting (FACS) has been employed to separate the gene-trapped cell population which shows green fluorescence after 488 mm UV light excitation. The enrichment of these gene trapping events were performed by cell sorting machine (Altra Cell Sorter, Beckman Courter Co, Miami Fla., USA) showed that 95% of cell population (FIG. 8) were fluorescence positive and gene trapped since the hrGFP expression can only occur after this hrGFP gene was integrated into a downstream of a cellular promoter. Furthermore, in theory, these hrGFP should be a fusion protein with a cellular protein in frame after splicing occurred to join cellular exons and hrGFP together. This hypothesis of splicing and fusion protein has been demonstrated by a construct pGT5T (FIG. 6) using a Zeocin-resistance protein to hrGFP after splicing and translation (FIG. 7). RNA transcripts of hrGFP in gene-trapped population were also detected by RT-PCR method (FIG. 9). These results demonstrate that gene trapping events can be monitored on translational level by FACS and transcription level by RT-PCR analysis in this experiment.

Figure 11:
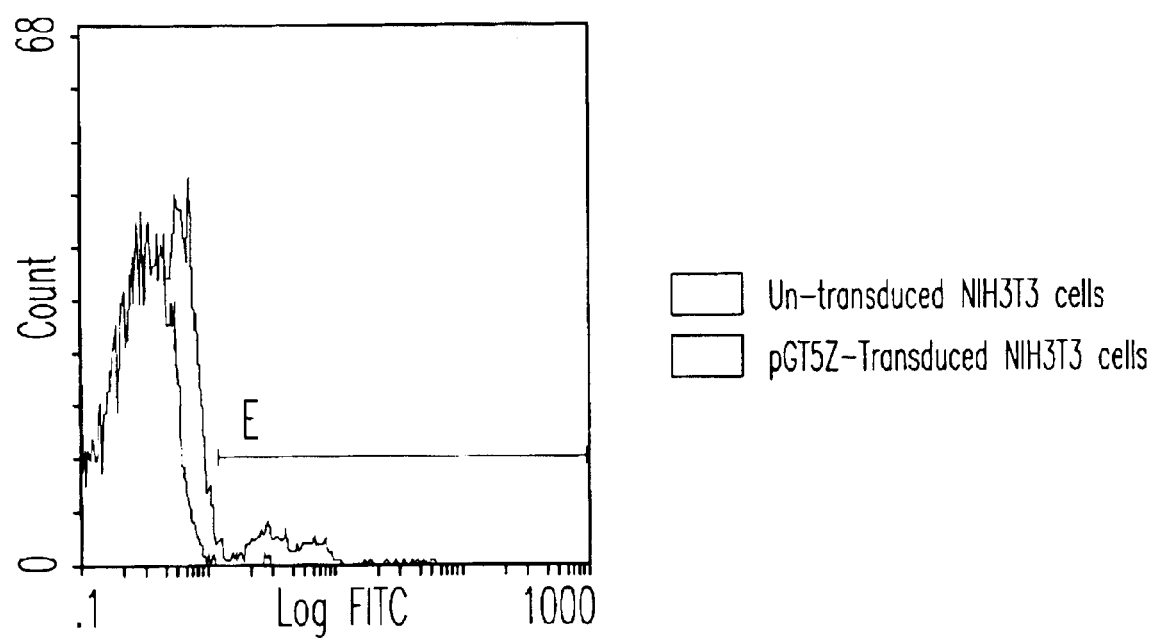
FIG. 11 is a depiction of gene trapping of GT5A vector in NIH3T3 cells. Mixed population of GT5A-trapped NIH3T3 cells were sorted and cultured for three weeks and then analyzed by FACS comparing to untransduced cells. Different intensities of hrGFP were shown in four different major groups.
Figure 12:
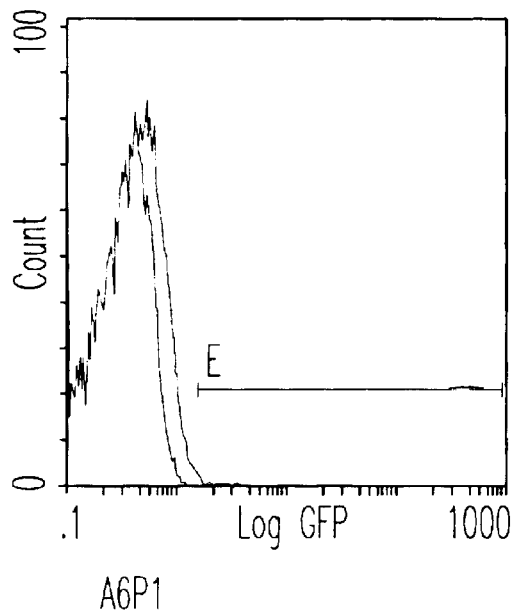
FIG. 12 is a depiction of hrGFP gene expression of single-cell clones from GT5A-trapped NIH3T3 cells. Individual single-cells were sorted into 96-wells plate and cultured to a sufficient population for FACS analysis. A6P1 and C4P2, C8P2 and H8P2 were analyzed at two different events while compared to untransduced NIH3T3 cells.
Figure 12:
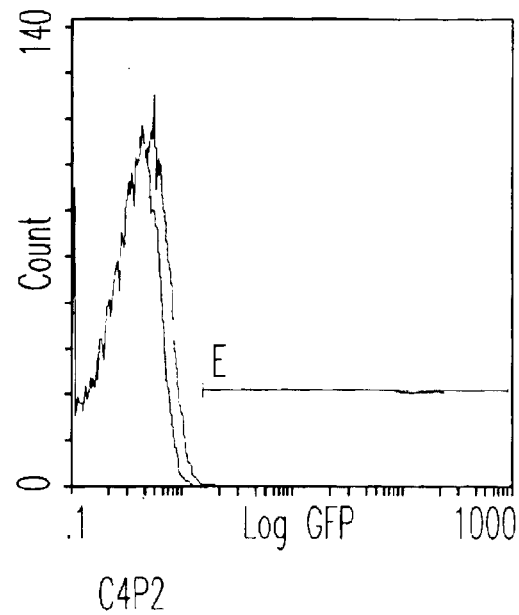
Figure 12:
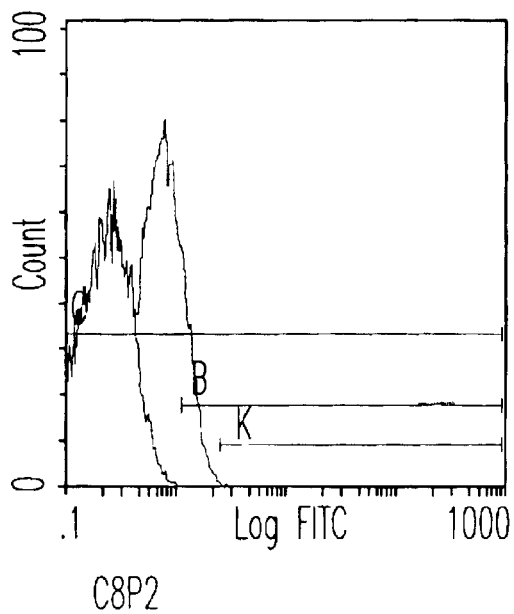
Figure 12:
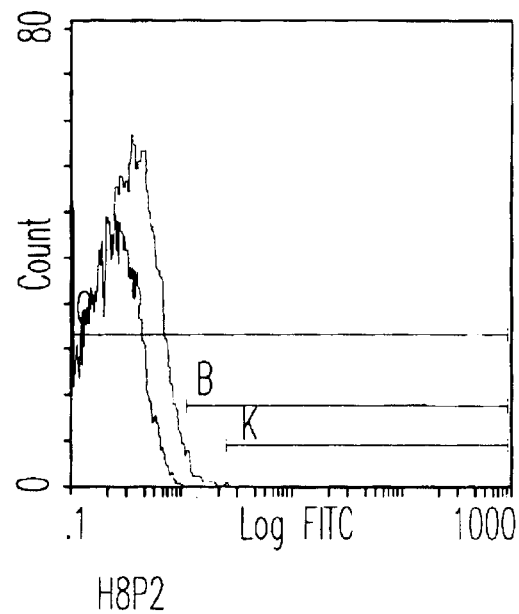

One important aspect of the invention is the high throughput platform to sort gene-trapped cells by using FACS which can sort 15,000 cells/second. The quantity and stability of trapped gene product, which is fused to hrGFP and becomes a hrGFP fusion protein, can be determined by the intensities of hrGFP in the cells in FACS analysis (FIGS. 11 and 12). The invention can therefore be applied to determine the cellular protein levels at high throughput manner and overlook most of the pathways of gene expression altered by the causes of diseases, such as cancer, viral infection, drug treatment and gene transfer in gene therapy or gene transfer research. Other reporter genes can be used to replace the hrGFP gene, in other experiment, rodent α1,3-galactosyltransferase gene, which is not expressed in a human cell, was used to demonstrate that gene trapping can be achieved by simple plasmid transfection in up to 1% of the population (FIG. 13C) as well as by retroviral vector infection (FIG. 13B). The results of this experiment are shown in FIGS. 20 and 21.

FIG. 20 is a depiction of a successful gene trapping in pGT5A-transfected PA317 cells. NcoI restriction site located at the 5' end of hrGFP marker gene and an EcoRI at the Oligo-dA primer were used as cloning sites for gene trapped sequence into a sequencing vector which was digested with NcoI and EcoRI. After BLAST searching against mouse EST database in GenBank, the sequence trapped by pGT5A is a 99% match to a high mobility group protein, HMGI-C, a nuclear phosphoprotein that contains three short DNA-binding domains (AT-hooks) and a highly acidic C-terminus.

Interest in this protein has recently been stimulated by three observations: the expression of the gene is cell-cycle regulated, the gene is rearranged in a number of tumors of mesenchymal origin and mice that have both HMGI-C alleles disrupted exhibit the pygmy phenotype. These observations suggest a role for HMGI-C in cell growth, more specifically, during fetal growth since the protein is normally only expressed in embryonic tissues. It is likely that the HMGI-C protein acts as an architectural transcription factor, regulating the expression of one or more genes that control embryonic cell growth. Since HMGI-C binds to the minor groove at AT-rich DNA this interaction could be a target for minor groove chemotherapeutic agents in the treatment of sarcomas expressing the rearranged gene. As can be seen, the invention successfully identified a potential oncogene with a demonstration of high translation level of this gene product indicated by high intensity of hrGFP fusion protein in FACS analysis (FIG. 8).

FIG. 21 is a depiction of gene trapping of an exon with unknown biological function in pGT5A-transfected PA317 cells. NcoI restriction site located at the 5' end of hrGFP marker gene and an EcoRI at the oligo-dA primer were used as cloning sites for gene trapped sequence into a sequencing vector which was digested with NcoI and EcoRI. After BLAST searching against the EST database in GenBank, the sequence trapped by pGT5A is 95% match to a NCI__CGAP__Li9 Mus musculus cDNA clones, BF539247.1/BF533319.1/ . . . etc., which have been found in the cDNA libraries from salivary gland and liver. As can be seen the invention successfully identified a gene without known biological function, but with a known high-level of protein production indicated by the fusion protein of this gene product and hrGFP in FACS analysis in FIG. 8. These results indicate that this invention can correlate the translation level of genes to some other unknown, or undefined DNA sequences for potential new discoveries of genes or targets responsible for diseases or cancers.

What is claimed is:

1. A method of elucidating a protein expression profile of a test cell line or group of cells, the method comprising:

(A) randomly introducing into the genome of a cell or group of cells a promoterless polynucleotide construct, the construct comprising in a 5' to 3' orientation:
  i) a splice acceptor consensus sequence;
  ii) the complementary sequence of a type IIS restriction enzyme recognition sequence;
  iii) an oligonucleotide sequence encoding assayable marker peptide; and
  iv) a polyadenylation sequence;

(B) wherein said promoterless polynucleotide construct when introduced into an actively expressed gene results in the generation of a truncated cellular protein fused at its C-terminal truncated end to the marker peptide; and
  i) identifying those cells expressing said marker peptide fused to said truncated cellular protein;
  ii) determining the identity of the truncated proteins to which the marker peptide is fused in each group of cells, thereby elucidating a protein expression profile of a test cell line of group of cells.

2. The method of claim 1 further comprising sorting cells identified in step (B)(i) into subpopulations based on their different levels of expression of said marker peptide.

3. The method of claim 1 wherein the identity of the protein to which the marker peptide is fused is determined using Serial Analysis of Viral Integration (SAVI).

4. The method of claim 3 wherein Serial Analysis of Viral Integration (SAVI) is performed by:
  i) isolating mRNA from each subgroup of cells;
  ii) reverse transcribing the mRNA into double stranded cDNA;
  iii) subjecting the cDNA to a restriction enzyme that recognizes the type IIS restriction enzyme recognition sequence, and cleaves the cDNA upstream of the recognition sequence, thereby generating one or more cDNA fragments, wherein each of these fragments comprise the oligonucleotide sequence corresponding to an upstream exon directly fused to the marker peptide, the type IIS restriction enzyme recognition sequence and a portion of a native sequence corresponding to the peptide marker;
  iv) adding an adaptor sequence to the end of the unknown oligonucleotide sequence;
  v) amplifying by the polymerase chain reaction, the fragments containing the oligonucleotide sequences of the exons fused to the marker peptide with oligonucleotide primers complementary to the adaptor and peptide marker encoding sequences;
  vi) cloning and sequencing said amplified fragments; and
  vii) comparing the sequence of each oligonuclcotide against oligonucleotide sequences in a one or more nucleotide sequence database thereby identifying one or more fusion proteins present in each subgroup of cells.

5. A method of identify differentially expressed proteins in two different populations of cells, the method comprising:

(A) randomly introducing into the genomes of a reference group of cells and into the genomes of a test group of cells a promoterless polynucleotide construct, wherein the construct comprises in a 5' to 3' orientation:
  i) a splice acceptor consensus sequence;
  ii) the complementary sequence of a type IIS restriction enzyme recognition sequence;
  iii) an oligonucleotide sequence encoding assayable marker peptide; and
  iv) a polyadenylation sequence;

(B) thereby generating a population of randomly truncated cellular proteins fused at their C-terminals truncated end to the marker peptide; and i) sorting both groups of cells into subpopulations of cells based on their differential expression levels of the marker peptide;

ii) determining the identity of the fusion proteins generated in each subgroup of sorted cells; and iii) comparing by statistical methods the protein expression profiles obtained for the test group of cells against the protein expression profiles obtained for the reference group of cells, thereby identifying differences in the expression levels of fusion proteins among the two groups of cells.

6. The method of claim 5 wherein the identity of the protein to which the marker peptide is fused is determined by SAVI.

7. The method of claim 4 or 6 wherein addition of the adaptor sequence is performed by ligation of a double stranded adaptor.

8. The method of claim 4 or 6, wherein addition of the adaptor sequence is performed by poly-deoxyribonucleotide tailing extension.

9. The methods of claim 3, 4 or 6 wherein following amplification of the one or more extended cDNA fragments, and prior to cloning and sequencing the one or more cDNA fragments, the fragments are ligated together to form a concatenated molecule.

10. The methods of claims 1, 5, or 6 where the peptide marker encoding sequence lacks a translation initiation codon and possesses a translation STOP codon.

11. The methods of claims 1, 5 or 6 where the peptide marker encoding sequence lacks a translation initiation and STOP codons.

12. The methods of claim 1, 5 or 6 wherein said separation of cells into subpopulations of cells based on the levels of expression of the peptide marker is performed by fluorescent activated cell sorting.

13. The methods of claims 1, 5 or 6 wherein marker peptide is an epitope recognized by fluorescently or enzymatically labeled antibodies.

14. The methods of claims 1, 5 or 6 wherein the marker peptide requires interaction with another protein in order to generate fluorescent signal.

15. The methods of claims 1, 5 or 6 wherein the polynucleotide construct further comprised, downstream of the oligonucleotide encoding a marker peptide and before the polyadenylation signal, an internal ribosome entry site followed by another protein expression marker.

16. The methods of claims 1, 5 or 6 wherein the polynucleotide construct further comprises, downstream of the oligonucleotide having a specified sequence, a sequence encoding, upon expression, a selectable marker.

17. The methods of claims 1, 5 or 6 wherein the oligonucleotide sequence is a fluorescent protein coding oligonucleotide sequence.

18. The methods of claim 17, wherein the fluorescent protein encoding oligonucleotide is a green fluorescent protein (GFP) coding sequence.

19. The method of claim 18, wherein the GFP oligonucleotide coding sequence is a humanized renilla GFP (hrGFP) coding sequence.

20. The methods of claims 1, 5 or 6 wherein the polynucleotide construct is introduced into the genome of the cell via a vector.

21. The methods of claim 20, wherein the vector is a viral vector.

22. The methods of claim 21, wherein the viral vector is selected from the group consisting of a retroviral vector, a lentiviral vector, an adenoviral vector and an adeno-associated viral vector.

* * * * *

UNITED STATES PATENT AND TRADEMARK OFFICE
CERTIFICATE OF CORRECTION

PATENT NO. : 6,897,020 B2
DATED : May 24, 2005
INVENTOR(S) : Charles J. Link et al.

It is certified that error appears in the above-identified patent and that said Letters Patent is hereby corrected as shown below:

Column 41,
Lines 26, 29 and 32, change "claims 1, 5," to -- claims 1-5, --;

Column 42,
Lines 1, 4, 7, 12, 16 and 25, change "claims 1, 5," to -- claims 1-5, --.

Signed and Sealed this

Seventh Day of February, 2006

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 375
<212> TYPE: DNA
<213> ORGANISM: Mus musculus
<220> FEATURE:
<223> OTHER INFORMATION: Sequence trapped demonstrates 99% homology to a
      high mobility group protein, HMGI-C after a BLAST search against
      moust EST database in Genbank.
<220> FEATURE:
<221> NAME/KEY: misc_feature
<222> LOCATION: (3)..(4)
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<222> LOCATION: (358)..(374)
<223> OTHER INFORMATION: n=unknown

<400> SEQUENCE: 1
ttnnccgnga aagctcctcg cccttgctca ccatgggatg ccatttccta ggtctgcctc      60
ttggccgttt ttctccaatg gtctctgctt tcttctgggc tgctttagag gggctcttgt     120
ttttgctgcc tttgggtctt cctctgggtc tcttaggaga gggctcacag gttggctctt     180
gctgctgctt cctgggtcgg ccgcgtcctc gcttctgtgg caccggggcg gcaggttgtc     240
cctgggctga tgtggacggc tgcccggcgc cctcaccgcg tgcgctcatc ctgcctcccg     300
ccgccgctac cactgcctct cttttttttt tttttttttt tttttgaaan ccccgggnnn     360
nnnnnnnnnn nnnnc                                                    375
```

-continued

```
<210> SEQ ID NO 2
<211> LENGTH: 333
<212> TYPE: DNA
<213> ORGANISM: Mus musculus
<220> FEATURE:
<223> OTHER INFORMATION: Gene trapping of an exon with unknown
      biological function;  the sequenced is a 95% match to a
      NCI_CGAP_Li 9 Mus musculus cDNA clones,
      BF539247.1/BF533319.1/...etc., after BLAST searching against the
      EST database in genebank.
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<222> LOCATION: (285)..(286)
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<222> LOCATION: (292)..(293)
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
```

-continued

```
<222> LOCATION: (306)..(308)
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<222> LOCATION: (326)..(327)
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown
<220> FEATURE:
<221> NAME/KEY: misc_feature
<223> OTHER INFORMATION: n=unknown

<400> SEQUENCE: 2
tcngcgacca nctcctcgcc cttgctcacc atgggatgct cccggtggtg ggtcggtggt      60
ccctgggcag gggtctccaa atcccggacg agcccccaaa tgaaanaccc ccgtcntggg     120
tagtcaatca ctcagaggag accctcccaa ggaacagcga gaccactntt cggatgcana    180
cagcaagagg ctttattggg aatncgggta cccgggcgac ncantctatc ngaagactgg    240
cgttattttt tttnttttt tttttgaat tnccnggac ancncnctna gnntancnc        300 nctntnnnct nccctcctta cttctnntnt ntn                                  333
```